(12) United States Patent
Carroll et al.

(10) Patent No.: US 6,706,880 B2
(45) Date of Patent: Mar. 16, 2004

(54) COCAINE RECEPTOR BINDING LIGANDS

(75) Inventors: Frank I. Carroll, Durham, NC (US); Michael J. Kuhar, Atlanta, GA (US); John W. Boja, Cuyahega Falls, OH (US); Anita H. Lewin, Chapel Hill, NC (US); Philip Abraham, Cary, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 09/956,159

(22) Filed: Sep. 20, 2001

(65) Prior Publication Data

US 2003/0023090 A1 Jan. 30, 2003

Related U.S. Application Data

(63) Continuation of application No. 09/083,043, filed on May 22, 1998, now Pat. No. 6,329,520, which is a continuation-in-part of application No. 08/706,263, filed on Sep. 4, 1996, now Pat. No. 6,531,483, which is a continuation-in-part of application No. 08/506,541, filed on Jul. 24, 1995, now abandoned, which is a continuation-in-part of application No. 07/972,472, filed as application No. PCT/US91/05553 on Aug. 9, 1991, now Pat. No. 5,413,779, said application No. 08/506,541, is a continuation-in-part of application No. 08/436,970, filed on May 8, 1995, now Pat. No. 5,736,123, and a continuation-in-part of application No. 08/164,576, filed on Dec. 10, 1993, now Pat. No. 5,496,953, which is a continuation-in-part of application No. 07/792,648, filed on Nov. 15, 1991, now abandoned, which is a continuation-in-part of application No. 07/564,755, filed on Aug. 9, 1990, now Pat. No. 5,128,118.

(51) Int. Cl.[7] .................. C07D 451/02; C07D 413/06; C07D 413/02; A61K 31/46
(52) U.S. Cl. ..................... 546/132; 546/124; 546/125; 546/94; 514/304; 514/235.2; 544/127
(58) Field of Search ............................ 546/124, 125, 546/132, 94; 514/304, 235.2; 544/127

(56) References Cited

U.S. PATENT DOCUMENTS

| | | | |
|---|---|---|---|
| 3,813,404 A | 5/1974 | Clark et al. | 260/292 |
| 5,128,118 A | 7/1992 | Carroll et al. | 424/1.1 |
| 5,186,921 A | * 2/1993 | Kung | 424/1.1 |
| 5,316,759 A | 5/1994 | Rose et al. | 424/10 |
| 5,374,636 A | 12/1994 | Moldt et al. | 514/304 |
| 5,380,848 A | 1/1995 | Kuhar et al. | 546/124 |
| 5,413,779 A | 5/1995 | Kuhar et al. | 424/1.85 |
| 5,444,070 A | * 8/1995 | Moldt | 514/304 |
| 5,496,953 A | 3/1996 | Kuhar et al. | 546/125 |
| 5,554,626 A | * 9/1996 | Moldt | 514/304 |
| 5,736,123 A | 4/1998 | Carroll | 424/1.85 |

FOREIGN PATENT DOCUMENTS

WO  WO 97/16451  5/1997

OTHER PUBLICATIONS

Maarten E.A. Reith, et al., "Structural Requirements for Cocaine Congeners to Interact with Dopamine and Serotonin Uptake Sites in Mouse Brain and to Induce Stereotyped Behaviro", Biochemical Pharmacology, vol. 35, No. 7, pp. 1123–1129, 1986.

G. K. Lloyd et al., "Neuronal Nicotinic Acetylcholine Receptors as Novel Drug Targets", The Journal of Pharmacology and Experimental Therapeutics, Perspectives in Pharmacology, Oct. 5, 1999, vol. 292, No. 2, pp. 461–467.

J. E. Rose et al., "Concurrent Agonist–Antagonist Administration for the Analysis and Treatment of Drug Dependence", Pharmacology Biochemistry & Behavior, Rapid Communication, 1991, vol. 41, pp. 219–226.

M. I. Damaj et al., "Pharmacological Characterization of Nicotine's Interaction with Cocaine and Cocaine Analogs", The Journal of Pharmacology and Experimental Therapeutics, Jan. 28, 1999, vol. 289, No. 3, pp. 1229–1236.

N. Lerner–Marmarosh et al., "Antagonism of Nicotine's Action by Cocaine Analogs", Life Sciences, Pharmacology Letters, Accelerated Communication, Oct. 25, 1994, vol. 56, No. 3, pp. 67–70.

C. G. V. Sharples et al., "UB–165: A Novel Nicotinic Agonist with Subtype Selectivity Implicates the α4β2 Subtype in the Modulation of Dopamine Release from Rat Striatal Synaptosomes", The Journal of Neurosclence, Apr. 15, 2000, vol. 20, No. 8, pp. 2783–2791.

A. H. Lewin et al., "Positive Identification and Quantitation of Isomeric Cocaines by High–Perfomrance Liquid Chromatography", Journal of Chromatography, Jan. 17, 1980, vol. 193, pp. 371–380.

A. Chang et al., "Synthesis and Transporter Binding Properties of 2,3–Diphenyltropane Stereoisomers. Comparison to 3β–Phenyltropane–2β–Carboxylic Acid Esters", Journal of Medicinal Chemistry, 1997, vol. 40, No. 8, pp. 1247–1251.

F. I. Carroll et al., "Syntheses and Conformational Analyses of Isomeric Cocaines: A Proton and Carbon–13 Nuclear Magnetic Resonance Study", The Journal of Organic Chemistry, 1982, vol. 47, No. 13, pp. 13–19.

A. H. Lewin et al., "A Practical Synthesis of (+)–Cocaine", Journal of Heterocyclic Chemistry, 1987, vol. 24, No. 19, pp. 19–21.

(List continued on next page.)

Primary Examiner—Evelyn Mei Huang
(74) Attorney, Agent, or Firm—Oblon, Spivak, McClelland, Maier & Neustadt, P.C.

(57) ABSTRACT

The invention relates to novel compounds which show high affinity for cocaine receptors in the brain, particularly dopamine and serotonin transporter sites. The compounds may be used as imaging or pharmaceutical agents, in the diagnosis and treatment of drug addiction, depression, anorexia and neurodegenerative diseases or in determining the doses of therapeutic agents that occupy significant numbers of receptors.

4 Claims, 9 Drawing Sheets

OTHER PUBLICATIONS

F. I. Carroll et al., "Cocaine Receptor–Design of Ligands", *Drugs of Abuse: Chemistry, Pharmacology, Immunology, and AIDS*, NIDA Monograph 96, 1990, pp. 112–121.

T. M. Naseree et al., "Sunthesis of [$^3$H]WIN 35,065–2; A New Radioligand for Cocaine Receptors", *Journal of Labelled Compounds and Radiopharmaceuticals*, 1989, vol. XXVIII, No. 9, pp. 1011–1016.

M. C. Ritz et al., "[$^3$H]WIN 35,065–2: A Lignad for Cocaine Receptors in Striatum", *Journal of Neurochemistry*, 1990, vol. 55, pp. 1556–1562.

J. W. Boja et al., "New, Potent Cocaine Analogs: Ligand Binding and Transport Studies in Rat Striatum", *European Journal of Pharmacology*, 1990, vol. 184, pp. 329–332.

M. J. Kuhar et al., "Imaging Neurotransmitter Uptake Sites in Brain", *Soc. Neurosci.*, 1990, 16, 746.

F. I. Carroll et al., "Important Compounds in the Cocaine Class: A Synthesis Overview", *Emerging Technologies and New Directions in Drug Abuse Research*, NIDA Research Monograph No. 112, 1991, pp. 284–299.

F. I. Carroll et al., "Synthesis and Receptor Binding of Cocaine Analogs", *Problems of Drug Dependence 1990*, NIDA Research Monograph 105, 1991, pp. 147–153.

F. I. Carroll et al., "Synthesis and Ligand Binding of Cocaine Isomers at the Cocaine Receptor", *Journal of Medicinal Chemistry*, 1991, vol. 34, pp. 883–886.

J. W. Boja et al., "[$^{125}$I]RTI–55: A Potent Ligand for Dopamine Transporters", *European Journal of Pharmacology*, 1991, vol. 194, pp. 133–134.

J. W. Boja et al., "Isothiocyanate Derivatives of Cocaine: Irreversible Inhibition of Ligand Binding at the Dopamine Transporter", *Molecular Pharmacology*, Nov. 28, 1990, vol. 39, pp. 339–345.

J. J. Woodward et al., "Cocaethylene Inhibits Dopamine Uptake and Produces Cocaine–Like Actions in Drug Discrimination Studies", *European Journal of Pharmacology*, 1991, vol. 197, pp. 235–236.

F. I. Carroll et al., "Synthesis, Ligand Binding, QSAR, and CoMFA Study of 3β–(p–Substituted Phenyl–Tropane–2β–Carboxylic Acid Methyl Esters", *Journal of Medicinal Chemistry*, 1991, vol. 34, No. 9, pp. 2719–2725.

R. L. Balster et al., "Potent Substituted–3β–Phenyltropane Analogs of Cocaine Have Cocaine–Like Discriminative Stimulus Effects", *Drug and Alcohol Dependence*, 1991, vol. 29, pp. 145–151.

F. I. Carroll et al., "[$^{123}$I]3β–(4–Iodophenyl) Tropan–2β–Carboxylic Acid Methyl Ester (RTI–55), A Unique Cocaine Receptor Ligand for Imaging the Dopamine and Serotonin Transporters In Vivo", *Medicinal Chemistry Research*, 1991, vol. 1, pp. 289–294.

R. B. Rothman et al., "Preliminary Evidence that GBR12909 is Less Effective Oat Elecating Mesolimbic Dopamine Function than Cocaine", *Problems of Drug Dependence*, Proceedings of the 53$^{rd}$ Annual Scientific Meeting, Committee on Problems of Drug Dependence, Inc., 1991, p. 338.

P. Abraham et al., "N–Modified Analogues of Cocaine: Synthesis and Inhibition of Binding to the Cocaine Receptor", *Journal of Medicinal Chemistry*, 1992, vol. 35, No. 1, pp. 141–144.

A. H. Lewin et al., "2β–Substituted Analogues of Cocaine. Synthesis and Inhibition of Binding to the Cocaine Receptor", *Journal of Medicinal chemistry*, 1992, vol. 35, No. 1, pp. 135–140.

F. I. Carroll et al., "Cocaine Receptor: Biochemical Characterization and Structure–Activity Relationships of Cocaine Analogues at the Dopamine Transporter", *Journal of Medicinal Chemistry*, 1992, vol. 35, No. 6, pp. 969–981.

F. I. Carroll et al., "Synthesis and Ligand Binding of 3β–(3–Substituted Phenyl)–and 3β–(3,4–Disubstituted Phenyl–Tropane–2β–Carboxylic Acid Methyl Esters", *Medicinal Chemistry Research*, 1992, vol. 1, pp. 382–387.

F. I. Carroll et al., "Probes for the Cocaine Receptor. Potentially Irreversibly Ligands for the Dopamine Transporter", *Journal of Medicinal Chemistry*, 1992, vol. 35, No. 10, pp. 1813–1817.

E. K. Shaya et al., "In Vivo Imaging of Dopamine Reuptake Sites in the Primate Brain Using Single Photon Emission Computed Tomography (SPECT) and Iodine–123 Labeled RTI–55", *Synapse*, 1992, vol. 10, pp. 169–172.

E. J. Cline et al., "Behavioral Effects of Novel Cocaine Analogs: A Comparison with In Vivo Receptor Binding Potency", *The Journal of Pharmacology and Experimental Therapeutics*, Dec. 2, 1991, vol. 260, No. 3, pp. 1174–1179.

A. Patel et al., "A Cocaine Analog and a GBR Analog Label the Same Protein in Rat Striatal Membranes", *Brain Research*, 1992, vol. 576, pp. 173–174.

J. W. Boja et al., "High Potency Cocaine Analogs: Neurochemical, Imaging, and Behavioral Studies", *Annals New York Academy of sciences*, pp. 282–291.

J. W. Boja et al., "High–Affinity Binding of [$^{125}$I]RTI–55 to Dopamine and Serotonin Transporters in Rat Brain", *Synapse*, 1992, vol. 12, pp. 27–36.

U. Scheffel et al., "[$^{123/125}$I]RTI–55, an In Vivo Label for the Serotonin Transporter", *Synapse*, 1992, vol. 11, pp. 34–39.

E. J. Cline et al., "Stimulus Generalization from Cocaine to Analogs with High In Vitro Affinity for Dopamine Uptake Sites", *Behavioural Pharmacology*, 1992, vol. 3, pp. 113–116.

M. C. Ritz et al., "Isopropyl and Phenyl Esters of 3β–(4–Substituted Phenyl)Tropan–2β–Carboxylic Acids. Potent and Selective Compounds for HTE Dopamine Transporter", *Journal of Medicinal Chemistry*, Communications to the Editor, 1992, vol. 35, No. 13, pp. 2497–2500.

J. F. Casale et al., "Base–Catalyzed C–2 Exchange and Epimerization of Cocaine Analogs: Methyl 3β–Substituted 8–Methyl–8–Azabicyclo[3.2.1]Octane–2–Carboxylates", *The Journal of Organic Chemistry*, 1992, vol. 57, No. 18, pp. 4906–4912.

E. J. Cline et al., "In Vivo Binding of [$^{125}$I]RTI–55 to Dopamine Transporters: Pharmacology and Regional Distribution with Autoradiography",*Synapse*, 1992, vol. 12, pp. 37–46.

U. Scheffel et al., "Dopamine Transporter Imaging with Novel Selective Cocaine Analogs", *NeuroReport*, Membrane and Cellular Biophysics and Biochemistry, Nov. 1992, vol. 3, No. 11, pp. 969–972.

J. W. Boja et al., "Selective Dopamine Transporter Inhibition by Cocaine Analogs", *NeuroReport*, Molecular Neuroscience, Nov. 1992, vol. 3, No. 11, pp. 984–986.

R. B. Rothman et al., "Cocaine and GBR12909 Produce Equivalent Motoric Responses at Different Occupancy of the Dopamine Transporter", *Pharmacology Biochemistry and Behavior, 1992*, 1992, vol. 43, pp. 1135–1142.

W. Rostène et al., "Dopamine Transport: Pharmacological Distinction Between the Synaptic Membrane and the Vesicular Transporter in Rat Striatum", *European Journal of Pharmacology*, 1992, vol. 218, pp. 175–177.

F. I. Carroll et al., "Pharmacophore Development of (−)–Cocaine Analogs for the Dopamine, Serotonin, and Norepinephrine Uptake Sites Using QSAR and CoVFA Approach", Supported in part by the National Institute on Drug Abuse, grant No. DA05477.

F. I. Carroll et al., "Cocaine Receptor: A Structure–Activity Relationship Study", *In Medications Development: Drug Discovery, Databases, and Computer–Aided Drug Design*, NIDA Research Monograph No. 134, 1993, pp. 229–237.

F. I. Carroll et al., "3β–(Substituted Phenyl_Tropan–2–Carboxylic Acid Ester Analogues of Cocaine", *Drug Design for Neuroscience*, New York, 1993, pp. 149–166.

F. I. Carroll et al., "Synthesis and Cocaine Receptor Affinities of 3–Phenyl–2–(3'–Methyl–1,2,4–Oxadiazole–5'–YL)Tropane Isomers", *Journal Chem. Society, Chemical Communication*, The Royal Society of Chemistry, 1993, Issue 1, pp. 44–46.

K. Y. Little et al., "[$^{125}$I]RTI–55 Binding to Cocaine–Sensitive Dopaminergic and Serotonergic Uptake Sites in the Human Brain", *Journal of Neurochemistry*, 1993, vol. 61, No. 6, pp. 1996–2006.

F. I. Carroll et al., "3–ARYL–2–(3'–Substituted–1', 2', 4'–Oxadiazol–5'–YL)Tropane Analogues of Cocaine" Affinities at the Cocaine Binding Site at the Dopamine, Serotonin, and Norepinephrine Transporters, *Journal of Medicinal Chemistry*, 1993, vol. 36, No. 20, pp. 2886–2890.

J. R. Lever et al., "Radiosynthesis of a Photoaffinity Probe for the Cocaine Receptor of the Dopamine Transporter: 3β–(p–Chlorophenyl)Tropan–2β–Carboxylic Acid m([$^{125}$I]– IODO)–p–Azidophenehyl Ester ([$^{125}$I]–RTI–82)", *Journal of Labelled Compounds and Radiopharmaceuticals*, 1993, vol. XXXIII, No. 12, pp. 1131–1137.

K. Y. Little et al., "Cocaine Use Increases [$^3$H]WIN 35428 Binding Sites in Human Striatum", *Brain Research*, 1993, vol. 638, pp. 17–25.

F. I. Carroll et al., "Hallucinogenic Agents: Drugs of Abuse as Neurochemical Tools", *Problems of Drug Dependence*, NIDA Research Monograph 140, Proceedings of the 55th Annual Scientific Meeting, College on Problems of Drug Dependence, Inc., 1993, pp. 94–98.

R. B. Rothman et al., "Studies of the Biogenic Amine Transporters. II. A Brief Study on the Use of [$^3$H] DA–Uptake–Inhibition to Transporter–Binding–Inhibition Ratios for the In Vitro Evaluation of Putative Cocaine Antagonists", *Life Sciences*, 1993, vol. 53, No. 17, pp. PL–267–PL–272.

M. J. Kuhar et al., "A Cocaine Receptor: Properties and Significance", *Biological Bassi of Substance Abuse*, Cell Biology, 1993, pp. 71–80.

F. I. Carroll et al., "3β–(4'Chlorophenyl)Tropan–2β–Carboxamides and Cocaine Amide Analogues: New High Affinity and Selective Compounds for the Dopamine Transporter" *Medicinal Chemistry Research*, 1993, vol. 3, pp. 468–472

C. M. Dersch et al., "Studies of the Biogenic Amine Transporters. 1. Dopamine Reuptake Blockers Inhibit [$^3$H]Mazindol Binding to the Dopamine Transporter by a Competitive Mechanism: Preliminary Evidence for Different Binding Domains", *Neurochemical Research*, 1994, vol. 19, No. 2, pp. 201–208.

J. W. Boja et al., "Secondary Amine Analogues of 3β–(4'–Substituted Phenyl)Tropane–2β–Carboxylic Acid Esters and N–Norcocaine Exhibit Enhanced Affinity for Serotonin and Norepinephrine Transporters", *Journal of Medicinal Chemistry*, 1994, vol. 37, No. 8, pp. 1220–1223.

F. I. Carroll et al., "Chemical Approaches to the Treatment of Cocaine Abuse", *Pharmaceutical News*, Technical Review, 1994, vol. 1, No. 2, pp. 11–17.

H. C. Akunne et al., "Studies of the Biogenic Amine Transporter. III. Demonstration of Two Binding Sites for [$^3$H]GBR12935 and [$^3$H]BTCP in Rat Caudate Membranes", *The Journal of Pharmacology and Experimental Therapeutics*, 1992, vol. 268, No. 3, pp. 1462–1475.

F. I. Carroll et al., "Synthesis, Ligand Binding, QSAR (CoMFA and Classical) Study of 3β–(3'–Substituted Phenyl)–, 3β–(4'–Substituted Phenyl)–, and 3β–(3', 4'–Disubstituted Phenyl)Tropane–2β–Carboxylic Acid Methyl Esters", *Journal of Medicinal Chemistry*, 1994, vol. 37, No. 18, pp. 2865–2873.

R. B. Rothman et al., "Studies of the Biogenic Amine Transporters. IV. Demonstration of a Multiplicity of Binding Sites in Rat Caudate Membranes for the Cocaine Analog [$^{125}$I]RTI–55", *The Journal of Pharmacology and Experimental Therapeutics*, 1994, vol. 270, No. 1, pp. 296–309.

D. Matecka et al., "Synthesis and Absolute Configuration of Chiral Piperazines Related to GBR 12909 as Dopamine Reuptake Inhibitors", *Medicinal Chemistry Research*, 1994, vol. 5, pp. 43–53.

F. I. Carroll et al., "Cocaine and 3β–(4'–Substituted Phenyl)Tropane–2β–Carboxylic Acid Ester and Amide Analogues. New High–Affinity and Selective Compounds for the Dopamine Transporter", *Journal of Medicinal Chemistry*, 1995, vol. 38, No. 2, pp. 279–388.

M. L. Silverthorn et al., "Studies of the Biogenic Amine Transporter. V. Demonstration of Two Binding Sites for the Cocaine Analog [$^{125}$I]RTI–55 Associated with the 5–HT Transporter in Rat Brain Membranes", *The Journal of Pharmacology and Experimental Therapeutics*, 1995, vol. 273, No. 1, pp. 213–222.

F. I. Carroll et al., "Development of Imaging Agents for the Dopamine Transporter", *Medicinal Research Reviews*, 1995, vol. 15, No. 5, pp. 419–444.

N. Lerner–Marmarosh et al., "Antagonism of Nicotine's Action by Cocaine Analogs", *Life Sciences*, Pharmacology Letters, Accelerated Communication, 1995, vol. 56, No. 3, pp. 67–70.

K. I. Keverline et al., "Synthesis if the 2β,3α– and 2β,3β–Isomers of 3–(p–Substituted Phenyl)Tropane–2–Carboxylic Acid Methyl Esters", *Tetrahedron Letters*, 1995, vol. 36, No. 18, pp. 3099–3102.

M. Stathis et al., "Rate of Binding of Various Inhibitors at the Dopamine Transporter In Vivo", *Psychopharmacology*, 1995, vol. 119, pp. 376–384.

N. D. Volkow et al, "Long–Lasting Inhibition of In Vivo Cocaine Binding T Dopamine Transporters by 3β–(4–Iodophenyl)Tropane–2–Carboxylic Acid Methyl Ester: RTI–55 or βCIT", *Synapse*, 1995, vol. 19, pp. 206–211.

R. B. Rothman et al., "Studies of the Biogenic Amine Transporters. VI. Characterization of a Novel Cocaine Binding Site, Identified with [$^{125}$I ]RTI–55, in Membranes Prepared from Whole Rat Brain Minus Caudate" *The Journal of Pharmacology and Experimental Therapeutics*, 1995, vol. 274, No. 1, pp. 385–395.

J. W. Boja et al., "Selective Labeling of the Dopmine Transporter by the High Affinity Ligand 3β–(4–[$^{125}$I] Iodophenyl)Tropane–2β–Carboxylic Acid Isopropyl Ester", *Molecular Pharmacology*, 1995, vol. 47, pp. 779–786.

J. K. Staley et al., "Mapping Dopamine Transporters in the Human Brain with Novel Selective Cocaine Analog [$^{125}$I] RTI–121", *Synapse*, 1995, vol. 21, pp. 364–372.

Pravin Kotian et al., "Synthesis and Ligand Binding Study of 3β(4'Substituted Phenyl)–3β–(Heterocyclic)Tropanes", J. Med. Chem., vol. 38, pp. 3451–3453, 1995.

Karley Y. Little et al., Characterization and Localization of [$^{125}$I]RTI–121 Binding Sites in Human Striatum and Medial Temporal Lobe[1,2].

John L. Musachio et al., "3β–(P–Trimethylsilyphenyl)Tropane–2β–Carboxylic Acid Methyl Ester: A New Precursor For the Preparation of [$^{123}$I]RTI–55", Appl. Radiat. Isot., Vol 47, No. 1, pp. 79–81, 1996.

S. John Gatley et al., "Displacement of RTI–55 from the Dopamine Transporter by Cocaine", European Journal of Pharmacology, vol. 296, pp. 145–151, 1996.

John R. Lever et al., Synthesis and in Vivo Studies of a Selective Ligand for the Dopamine Transporter: 3β–(4–[$^{125}$I]Iodophenyl) Tropan–2β–Carboxylic Acid Isopropyl Ester ([$^{125}$I]RTI–121), Nuclear Medicine & Biology, vol. 23, pp. 277–284, 1996.

Pravin Kotian et al., "Synthesis, Ligand Binding, and Quantitative Structure– Activity Relationship Study of 3β–(4'–Substituted Phenyl)–2β–Heterocyclic Tropanes: Evidence for an Electrostatic Interaction at the 2β–Position", J. Med. Chem., vol. 39, pp. 2753–2763, 1996.

Susan P. Hume et al., "Evaluation of [$^{11}$C]RTI–121 as a Selective Radioligand for Pet Studies of the Dopamine Transporter", Nuclear Medicine & Biology, vol. 23, pp. 377–384, 1996.

Bruce E. Blough et al., "Synthesis and Transportere Binding Properties of 3β–(4'–Alkyl–, 4'–Alkenyl–, and 4'–Alkynlyphenyl)Nortropane–2β–Carboxylic Acid Methyl Esters: Serotonin Transporter Selective Analogs", J. Med. Chem., vol. 39, pp. 4027–4035, 1996.

Christopher R. Holmquist et al., "3α–(4'Substituted Phenyl)Tropane–2β–Carboxylic Acid Methyl Esters: Novel Ligands with High Affinity and Selectivity at the Dopamine Transporter", J. Med. Chem., vol. 39, pp. 4139–4141, 1996.

Karley Y. Little et al., "Lack of Dopamine Receptor Agonists Effect on Striatal Dopamine Transporter Binding Sites", Brain Research, vol. 742, pp. 313–316, 1996.

Annette E. Fleckenstein et al., "Recovery of Dopamine Transporter Binding a Function After Intrastriatal Administration of the Irreversible Inhibitor RTI–76 {3β–(3p–Chlorophenyl)Tropan–2β–Carboxylic Acid P–Isothiocyanatophenylethyl Ester Hydrochloride}[1]", The Journal of Pharmacology and Experimental Therapeutics, vol. 279, pp. 200–206, 1996.

G.I. Elmer et al., "Cocaine Cross–Sensitization to Dopamine Uptake Inhibitors: Unique Effects of GBR12909", Pharmacology Biochemistry and Behavior, vol. 53, No. 4, pp. 911–918, 1996.

Annette E. Fleckenstein et al., "Highly Potent Cocaine Analogs Cause Long–Lasting Increases in Locomotor Activity", European Journal of Pharmacology, vol. 311, pp. 109–114, 1996.

Michael J. Kuhar et al., "Imaging Transporters for Dopamine and Other Neurotransmitters in Brain", Neurotransmitter Transporter: Structure, Function, and Regulation, Ed: M.E.A. Reith Humana Press, Inc., Totowa, NJ., pp. 297–313, 1997.

F. Ivy Carroll et al., "Dopamine Transporter Uptake Blockers", Neurotransmitter Transporter: Structure, Function, and Regulation, Ed: M.E.A. Reith Humana Press, Inc., Totowa, NJ., pp. 263–295, 1997.

Yougen Zhan et al., "TRI–352: A 3α Analogue of TRI–55 as an In Vivo Dopamine Transporter Binding Ligand", Synapse, vol. 25, pp. 389–392, 1997.

Karley Y. Little et al., "Serotonin Transporter Binding Sites and mRNA Levels in Depressed Persons Committing Suicide", Society of Biological Psychiatry, vol. 41, pp. 1156–1164, 1997.

Mohan Thiruvazhi et al., "Synthesis of the Isomers of (1R)–3–(Phenylthio)Tropane–2–Carboxylic Acid Methyl Ester. A New Class of Ligands for the Dopamine Transporter", Chem. Commun., pp. 555–556 1997.

Bruce E. Blough et al., "3β–(4–Ethyl–3–Iodophenyl)Nortropane–2β–Carboxylic Acid Methyl Ester as a High–Affinity Selective Ligand for the Serotonin Transporter", Journal of Medicinal Chemistry, vol. 40, No. 24, pp. 3861–3864, 1997.

Ursula Scheffel et al., "N–Substituted Phenyltropanes as in vivo Binding Ligands for Rapid Imaging Studies of the Dopamine Transporter", Synapse, vol. 25, pp. 345–349, 1997.

Richard B. Rothman et al., "Studies of the Biogenic Amine Transporters. VII. Characterization of a Novel Cocaine Binding Site Identified With [$^{125}$I]RTI–55 in Membranes Prepared from Human, Monkey and Guinea Pig Caudate", Synapse, vol. 28, pp. 322–338, 1998.

Steven I. Dworkin et al., "RTI–113 Administration Reduces Cocaine Self–Administration at High Occupancy of Dopamine Transporter", Synapse, vol. 30, pp. 49–55, 1998.

Kathryn I. Keverline–Frantz et al., "Synthesis and Ligand Binding of Tropane Ring Analogues of Paroxetine", Journal of Medicinal Chemistry, vol. 41, No. 2, pp. 247–257, 1998.

J.W. Boja et al., "Multiple Binding Sites for [$^{125}$i]RTI–121 and Other Cocaine Analogs in Rat Frontal Cerebral Cortex", Synapse, vol. 30, pp. 9–17, 1998.

C.D. Cook et al., Separation of the Locomotor Stimulant and Discriminative Stimulus Effects of Cocaine by its C–2 Phenyl Ester Analog, RTI–15, Drug and Alcohol Dependencies, vol. 50, pp. 123–128, 1998.

F. Ivy Carroll et al., "3β–Phenyl–2β–Substituted Tropanes–an SAR Analysis", Med. Chem. Res., vol. 8:1/2, pp. 59–65, 1998.

Karley Y. Little et al., "Striatal [$^{125}$]RTI–55 Binding Sites in Cocaine–Abusing Humans", Prog. Neuro–Physchopharmacol. & Biol. Psychiat., vol. 22, pp. 455–466, 1998.

Songchun Jiang et al. "Synthesis and Transporter Binding Properties of (R)–2β,3β– and (R)2α–3α–Diaryltropanes", Biorganic & Medicinal Chemistry Letters, vol. 8, pp. 3689–3692, 1998.

Maarten E. A. Reith et al., "[17] Inhibition of [$^3$H]Dopamine Translocation and [$^3$H]Cocaine Analog Binding: A Potential Screening Device for Cocaine Antagonists", Methods in Enzymology, vol. 296, pp. 248–259, 1998.

F. Ivy Carroll et al., "Pharmacotherapies for Treatment of Cocaine Abuse: Preclinical Aspects", Journal of Medicinal Chemistry, Vo. 41, No. 15, pp. 2721–2736, 1999.

Sari Izenwasser et al., "Continuous Infusion of Selective Dopamine Uptake Inhibitors or Cocaine Produces Time–Dependent Changes in Rat Locomotor Activity", Behavioural Brain Research, vol. 99, pp. 201–208, 1999.

Desong Zhong et al., "Synthesis of 3β–(4–[$^{125}$I]Iodophenyl)Tropane–2β–Pyrrolidine Carboxamide ([$^{125}$I]RTI–229)", Journal of Labelled Compounds and Radiopharmaceuticals, vol. 42, pp. 281–286, 1999.

Michael J. Kuhar et al., "Studies of Selected Phenyltropanes at Monoamine Transporters", Drug and Alcohol Dependencies, vol. 56, pp. 9–15, 1999.

Aleksandra Vicentic et al., "Serotonin Transporter Production and Degradation Rates: Studies with RTI–76", Brain Research, vol. 841, pp. 1–10, 1999.

Desong Zhong et al., "Synthesis of [$^{125}$I]–3β–(4–Ethyl–3–Iodophenyl)Nortropane– 2β–Carboxylic Acid Methyl Ester ([$^{125}$I]EINT)", Journal of Labelled Compounds and Radiopharmaceuticals, vol. 43, pp. 137–146, 2000.

Leonard L. Howell et al., "Comparative Behavioral Pharmacology of Cocaine and the Selective Dopamine Uptake Inhibitor RTI–113 in the Squirrel Monkey", The Journal of Pharmacology and Experimental Therapeutics, Vo. 292, No. 2, pp. 521–529, 2000.

* cited by examiner

SCHEME 2. Synthesis of Nitriles and Tetrazoles

RTI-163 X=Cl
RTI-157 X=CH3

RTI-161 X=Cl
RTI-158 X=CH3

SCHEME 3. Synthesis of Isoxazoles

RTI-165 X=Cl, R=CH3
RTI-171 X=CH3, R=CH3
RTI-180 X=I, R=CH3
RTI-177 X=Cl, R=Ph
RTI-176 X=CH3, R=Ph
RTI-181 X=I, R=Ph

COCAINE RECEPTOR BINDING LIGANDS

This application is a Continuation of U.S. application Ser. No. 09/083,043, filed on May 22, 1998, now allowed U.S. Pat. No. 6,329,520; which is a Continuation-in-Part application of U.S. application Ser. No. 08/706,263, filed Sep. 4, 1996, now U.S. Pat. No. 6,531,483, which is a Continuation-in-Part of U.S. application Ser. No. 08/506,541, filed Jul. 24, 1995, now abandoned; which is a Continuation-in-Part of (1) U.S. application Ser. No. 07/972,472, filed Mar. 23, 1993, which issued May 9, 1995 as U.S. Pat. No. 5,413,779 which is a U.S. PCT Application PCT/US91/05553 filed Aug. 9, 1991, filed in the U.S. PCT Receiving Office and designating the United States; (2) U.S. application Ser. No. 08/436,970, filed May 8, 1995; now U.S. Pat. No. 5,736,123; and U.S. application Ser. No. 08/164,576, filed Dec. 10, 1993, which issued Mar. 5, 1996 as U.S. Pat. No. 5,496,953; which is in turn a Continuation-in-Part of U.S. application Ser. No. 07/792,648, filed Nov. 15, 1991, now abandoned; which is in turn a Continuation-in-Part of U.S. application Ser. No. 07/564,755, filed Aug. 9, 1990, which issued Jul. 7, 1992 as U.S. Pat. No. 5,128,118; all of which are incorporated herein by reference in their entirety.

FIELD OF THE INVENTION

This invention is directed to a class of binding ligands for cocaine receptors, neurotransmitter transporters and other receptors, neurotransmitter transporters in the brain. Specifically, a novel family of compounds shows high binding specificity and activity, and, in a radiolabeled form, can be used to bind to these receptors, for biochemical assays and imaging techniques. Such imaging is useful for determining effective doses of new drug candidates in human populations. In addition, the high specificity, slow onset and long duration of the action of these compounds at the receptors makes them particularly well suited for therapeutic uses, for example as substitute medication for psychostimulant abuse. Some of these compounds may be useful in treating Parkinson's Disease, attention deficit hyperactivity disorder, bipolar disorder, eating disorders, obesity, panic attacks and disorders, obsessive-compulsive disorder, cocaine, nicotine and alcohol addiction or depression, by virtue of their inhibitory properties at monoamine transporters.

DISCLOSURE OF PARENT APPLICATIONS

This application claims priority, inter alia, from of U.S. patent application Ser. No. 07/972,472 filed Mar. 23, 1993, now U.S. Pat. No. 5,413,779, the entirety of which is incorporated by reference. This application also claims priority from U.S. patent application Ser. No. 07/564,755, now U.S. Pat. No. 5,128,118, and U.S. PCT Application PCT/US91/05553 (the U.S. National Phase of which is U.S. Ser. No. 07/972,472), filed Aug. 9, 1991, both applications being incorporated herein by reference. In U.S. application Ser. No. 07/564,755, there is disclosure of a family of compounds exhibiting particularly high specificity and affinity for cocaine receptors and other neurotransmitter receptors in the brain of the formula:

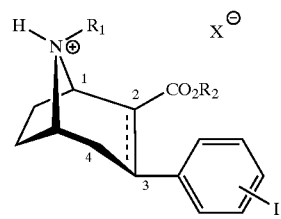

Where the broken line represents an optional chemical bond and the substituents at 2 and 3 may be at any position;

The iodo substituent may be at o, m, A, or multisubstituted;

$R_1$=$CH_3$, $CH_2CH$=$CH_2$, $(CH_2)_nC_6H_5$ n=1–4;
$R_2$=$CH_3$, $C_2H_5$, $CH_3(CH_2)_3$, $(CH_3)_2CH$, $C_6H_5$, $C_6H_5CH_2$, $C_6H_5(CH_2)_2$;
X=pharmacologically acceptable anion Sites of specific interest included cocaine receptors associated with dopamine (DA) transporter sites.

Subsequently, in the U.S. PCT Application from which priority is claimed, and which is incorporated herein by reference, the values for $R_1$ and $R_2$ were expanded, such that $R_1$ may be an alkyl of 1–7 carbon atoms, $CH_2CR_3$=$CR_4R_5$ wherein $R_3$–$R_5$ are each, independently $C_{1-6}$ alkyl, or phenyl compounds of the formula $C_6H_5(CH_2)_y$, wherein y=1–6. $R_2$ may be any of those list above and also $C_6H_5(CH_2)_z$, wherein z=1–6. The PCT filing also reveals the affinity of these compounds for cocaine receptors associated with serotonin (5-hydroxytryptamine, 5-HT) transporters, and confirms, for the first time, that the in vitro binding reported in the earlier-filed application, is confirmed in in vivo testing. Specific disclosure for a variety of applications, including using the compounds in both PET and SPECT scanning, wherein either the iodine substituent, or one of the carbon groups is radioactive (I-123, 125 or 131 and C-11) thus providing methods for scanning for the presence of specific cocaine receptors. Such scanning processes may be used to determine physiological conditions associated with dopamine and serotonin re-uptake inhibitors, which are or lead to behavioral and neurodegenerative disorders/diseases. Such disorders include depression, bipolar disorder, eating disorders, obesity, attention deficit disorder, panic attacks and disorders, obsessive-compulsive disorder, Parkinson's Disease, and cocaine, nicotine and alcohol addiction. These compounds, in addition to being used in treatment of these disorders, may be used to examine in general the density and distribution of specific cocaine receptors in various parts of the brain and/or body, to determine the efficacy of neurological treatments aimed at halting or reversing the degeneration of specific nerves in the brain, and for screening drugs, such as antidepressant drugs. The imaging techniques may also be used to determine the doses of novel or potential therapeutic agents that occupy significant quantities of receptors by in vivo competition technique.

The affinity and specificity of these compounds, as reported in the applications incorporated, is surprisingly high, and compared with prior art compounds, such as [$^3$H]WIN 35,428, the novel compounds of these applications exhibit extremely low $IC_{50}$ values for binding inhibition.

In U.S. patent application Ser. No. 08/164,576, filed Dec. 10, 1993, now U.S. Pat. No. 5,496,953, also incorporated herein by reference in its entirety, a family of compounds was disclosed, having the formula:

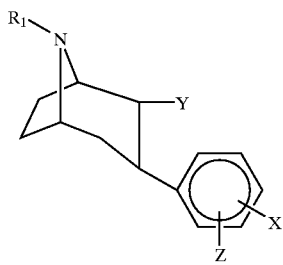

wherein
Y is $CONRR_2$,
$R_1$ is hydrogen or $C_{1-5}$ alkyl,
X is H, $C_{1-6}$ alkyl, $C_{3-8}$ cycloalkyl, $C_{1-4}$ alkoxy, $C_{1-6}$ alkynyl, halogen amino or acylamido,
R and $R_2$ independently are H, $C_{1-6}$ alkyl, alkene or alkyne, phenyl, phenyl substituted with 1–3 of $C_{1-6}$ alkyl, alkene, alkyne or alkoxy, $C_{1-6}$ alkoxy, phenoxy, amine amino substituted with 1 or 2 $C_{1-6}$ alkyl, alkene, alkyne, alkoxy, phenyl or phenoxy, or R and $R_2$ may combine to form a cyclic structure selected from the group consisting of pyrrolidinyl, morpholinyl and piperidinyl moieties, and
Z is H, I, Br, Cl, F, CN, $CF_3$, $NO_2$, $N_3$, $OR_1$, $CO_2NH_2$, $CO_2R_1$, $C_{1-6}$ alkyl, $NR_4R_5$, $NHCOF_5$, $NHCOR_6$, wherein $R_4$–$R_6$ are each $C_{1-6}$ alkyl.

These compounds exhibit unusually high affinity and specificity for binding to receptors for the dopamine transporter site, as well as the serotonin transporter site, based on inhibition of [$^3$H]paroxetine binding. This high affinity makes certain of these compounds particularly well suited for use as therapeutic agents, as well as for imaging agents for dopamine and serotonin transporters.

SUMMARY OF THE INVENTION

Accordingly, one object of this invention is to provide novel compounds which bind to cocaine receptors which include neurotransmitter transporters.

Another object of the invention is to provide novel 3-(substituted phenyl)-2-(substituted)tropane analogs which bind to cocaine receptors.

Still another object of the invention is to provide 3-(substituted phenyl)-2-(substituted)tropane analogs which bind preferentially to the dopamine transporter.

Yet another object of the invention is to provide 3-(substituted phenyl)-2-(substituted)tropane analogs which bind preferentially to the serotonin transporter.

Another object of the invention is to provide a compound of the formula

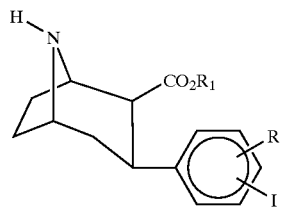

wherein R is $CH_3$, $C_2H_5$, $CH_2CH_2CH_3$, or $CH(CH_3)_2$, $R_1$ is $CH_3$, $CH_2CH_5$, $(CH_2)_2C_6H_5$, $(CH_2)_3C_6H_5$, or

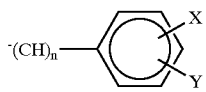

wherein X is H, $OCH_3$, or Cl and Y is H, $OCH_3$, $CO_2CH_3$ or Cl, and n=1–8.

Another object of the invention is to provide compounds having the following formulas:

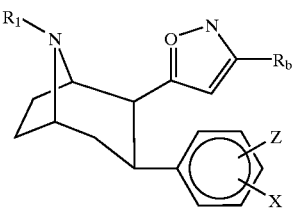

wherein
$R_1$=hydrogen, $C_{1-5}$ alkyl,
X=H, $C_{1-6}$ alkyl, $C_{3-8}$ cycloalkyl, $C_{1-4}$ alkoxy, $C_{1-6}$ alkynyl, halogen, amino, acylamido, and
Z=H, I, Br, Cl, F, CN, $CF_3$, $NO_2$, $N_3$, $OR_1$, $CONH_2$, $CO_2R_1$, $C_{1-6}$ alkyl, $NR_4R_5$, $NHCOR_5$, $NHCO_2R_6$,
$R_b$ is $C_{1-6}$ alkyl, $C_{1-6}$ alkenyl, phenyl, or phenyl substituted with $C_{1-6}$ alkyl, $C_{1-6}$ alkoxy, or halogen;

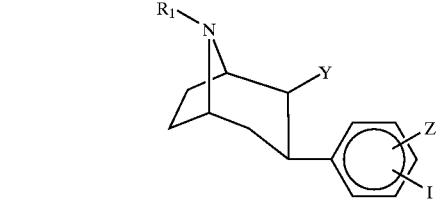

$R_1$, Y, and Z are as defined above and Z may additionally be

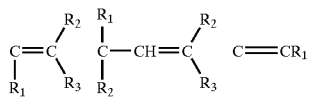

$R_1$, $R_2$, $R_3$ = H OR $C_{1-4}$ alkyl

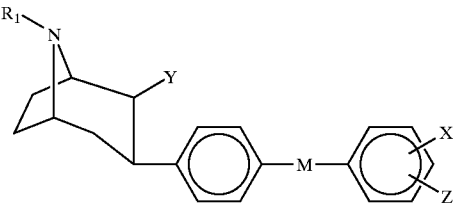

$R_1$, X, Y, Z are defined above and M = $(CH_2)_{1-8}$ or
C≡C or HC=CH

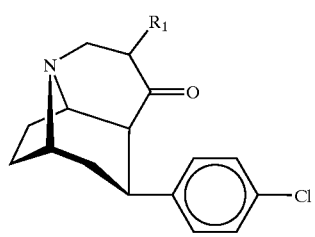

wherein $R_1$=H or $CO_2CH_3$;

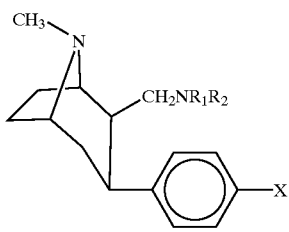

wherein $R_1$, $R_2$=H or $CH_3$ and X=$CH_3$;

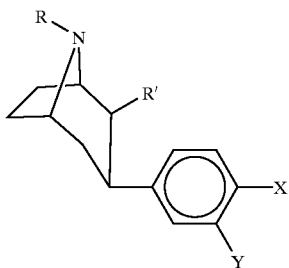

wherein R=H, $CH_3$ or $CH_2CO_2C_2H_5$,

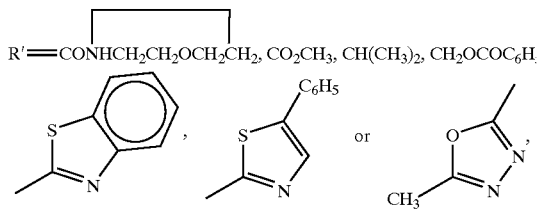

and Y=H, X=$CH_3$, Cl, t-$CH_3CH$=CH—, 2-naphthyl, or $H_2C$=C—;

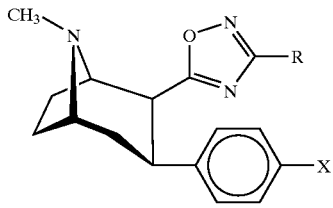

wherein R=$CH_3$, $C_6H_5$, 4-$CH_3OC_6H_4$, 4-$ClC_6H_4$, 4-$BrC_6H_4$, or $(CH_3)_2CH$ and X=Cl, $CH_3$ or H; and

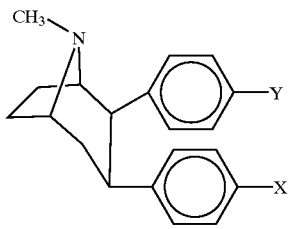

wherein X=$CH_3$ or H and Y=H or $CH_3$.

A further object of the invention is to provide a method for treating psychostimulant abuse, by administering to a patient in need of such treatment a pharmaceutically effective amount of a 3-(substituted phenyl)-2-(substituted)tropane analog.

A still further object of the invention is to provide method for inhibiting the action of a psychostimulant, by administering to a patient in need of such treatment a psychostimulant-inhibiting amount of a 3-(substituted phenyl)-2-(substituted)tropane analog.

Still another object of the invention is to provide a method for inhibiting neurotransmitter re-uptake by administering to a patient in need of such treatment a neurotransmitter transporter-inhibiting amount of a 3-(substituted phenyl)-2-(substituted)tropane analog.

Another object of the invention is to provide a method for treating neurodegenerative disorders, by administering to a patient in need of such treatment a pharmaceutically effective amount of a 3-(substituted phenyl)-2-(substituted) tropane analog.

A further object of the invention is to provide binding ligands for in vitro or in vivo studies, to measure doses, concentrations and receptor occupancy, or to screen for new drugs acting at these sites.

Still another object of the invention is to provide a method for treating depression, by administering to a patient in need of such treatment a pharmaceutically effective amount of a 3-(substituted phenyl)-2-(substituted)tropane analog.

Briefly, the invention pertains to the discovery that certain cocaine analogs are particularly well suited for therapeutic use as neurochemical agents. These particular cocaine analogs, in modulating neurotransmitter actions, may also be useful for modulating the actions of pyschostimulant drugs, for modulating endocrine function, for modulating motor function, and for modulating complex behaviors.

With the foregoing and other objects, advantages and features of the invention that will become here in after apparent, the nature of the invention may be more clearly understood by reference to the following detailed description of the preferred embodiments of the invention and to the appended claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

The present invention includes novel compounds having the following formula:

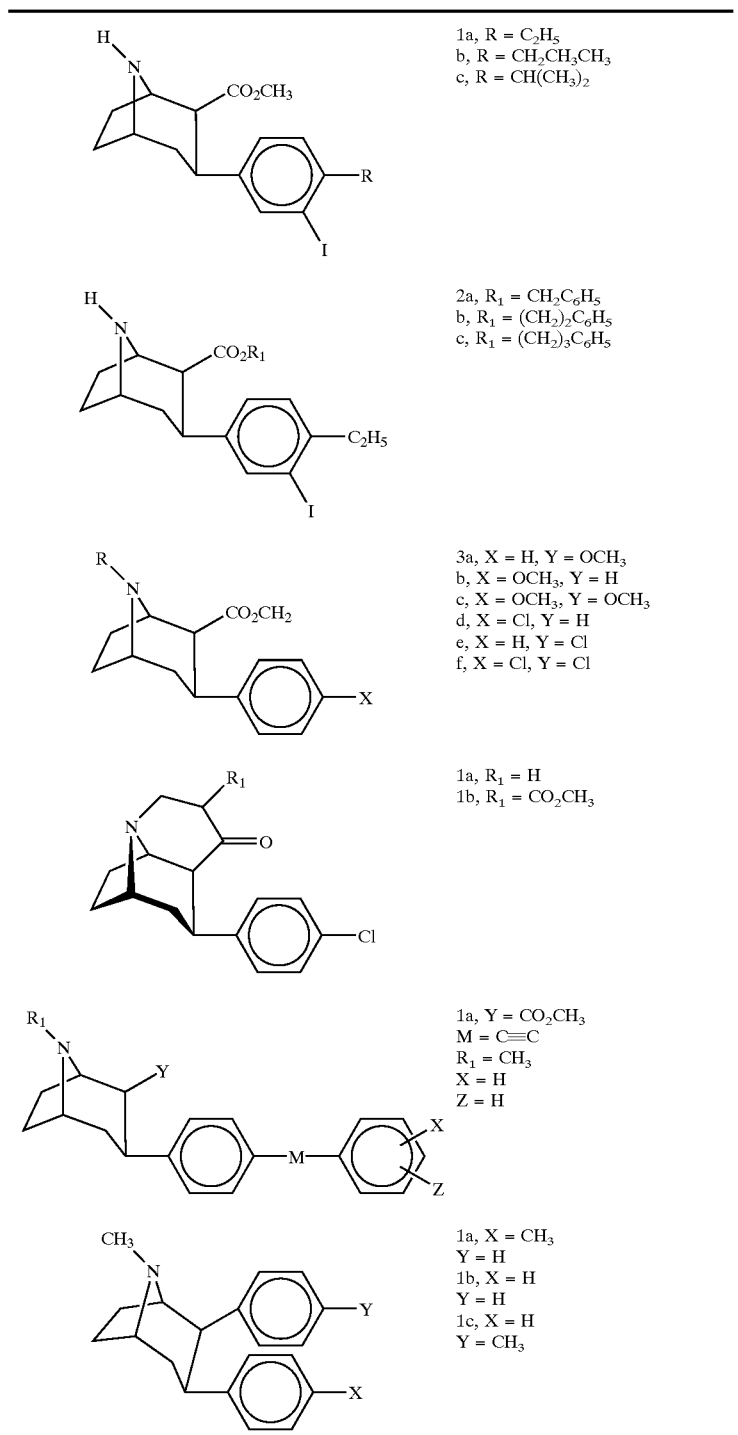

-continued
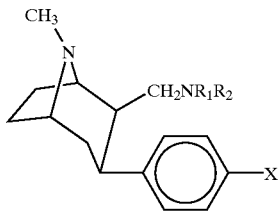
1a, R₁, R₂, X = CH₃
1b, R₁, X = CH₃
R₂ = H
1c, R₁, R₂ = H
X = CH₃
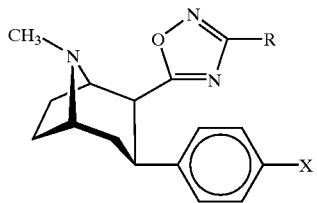
1a, R = C₆H₄
X = Cl
1b, R = 4-CH₃OC₆H₄
X = Cl
1c, R = C₆H₅
X = CH₃
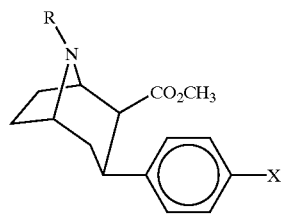
1a, R = CH₃,
X = t-CH₃CH=CH
1b, R = CH₃,
X = CH₃C≡C
1c, R = H,
X = HC≡C
1d, R = CH₂CO₂C₂H₅,
X = Cl
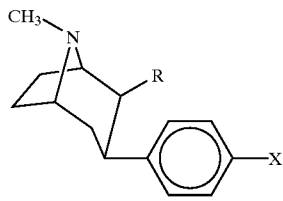
1a, R = CONCH₂CH₂OCH₂CH₂
X = Cl
1b, R = CON(CH₃)₂
X = Cl
1c, R = CH(CH₃)₂
X = CH₃
1d, R =
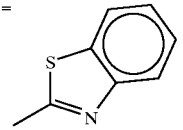
X = Cl
1e, R =
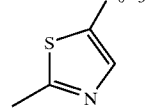
X = Cl
1f, R =
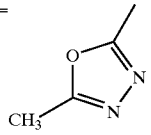
X = CH₃
1g, R = CH₂OCOC₆H₅
X = Cl The compounds of this invention can be prepared according to the synthesis methods described in the parent applications. Alternative synthesis for related compounds will be apparent to those of ordinary skill in the art. Particular synthesis schemes are exemplified in U.S. Pat. No. 5,444,070, which is incorporated herein in its entirety. Additional schemes follow hereinbelow.

Preparation of 3β-(Substituted phenyl)tropane-2β-heterocyclic Analogues

Chemistry

Figure 1:
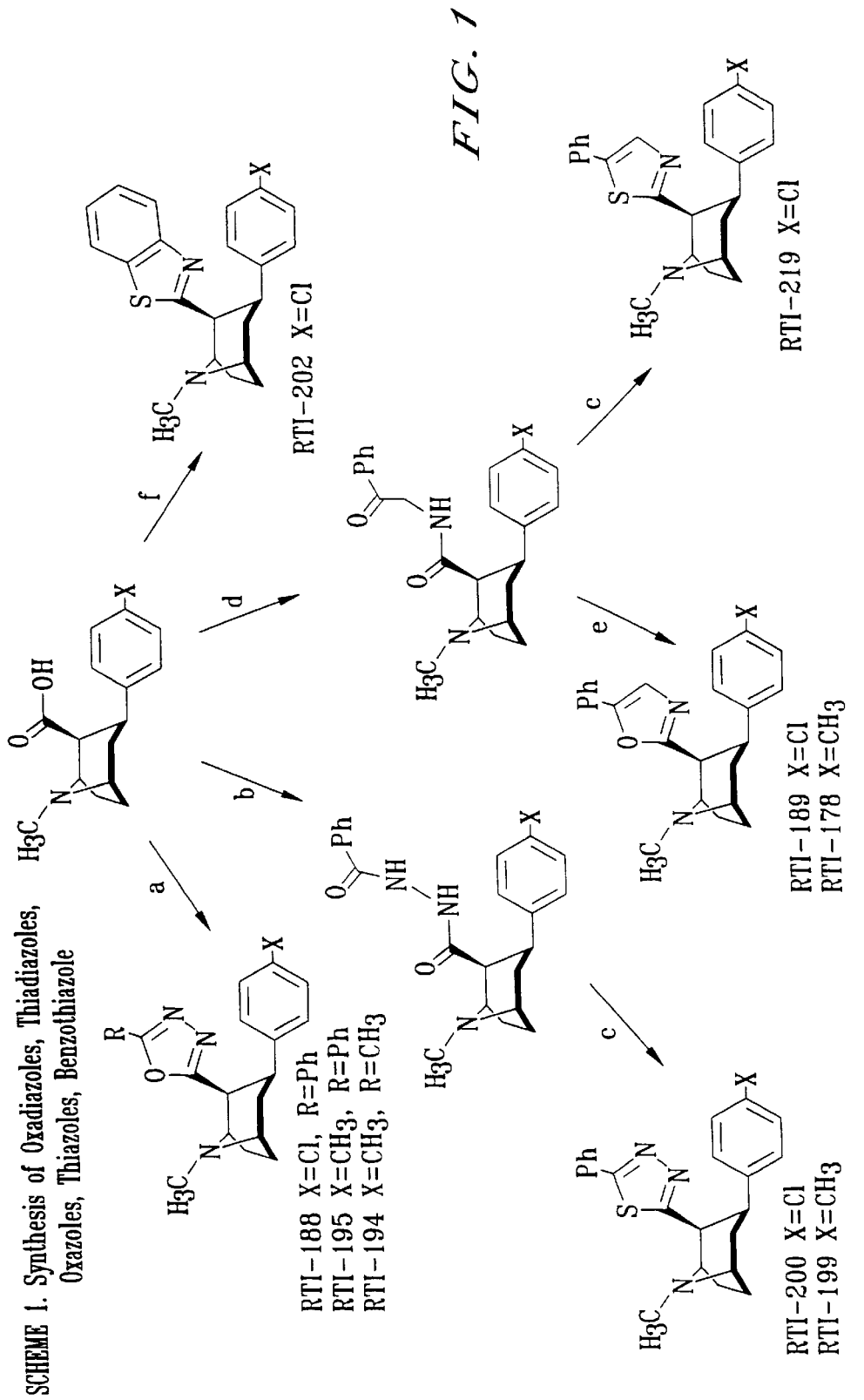
FIG. 1 depicts the scheme or converting 3-(substituted phenyl)-2-tropane carboxylic acid (tropane acid) to 2-substituted oxazoles, oxadiazoles, thiazoles, thiadiazoles and benzothiazole.
Figure 2:
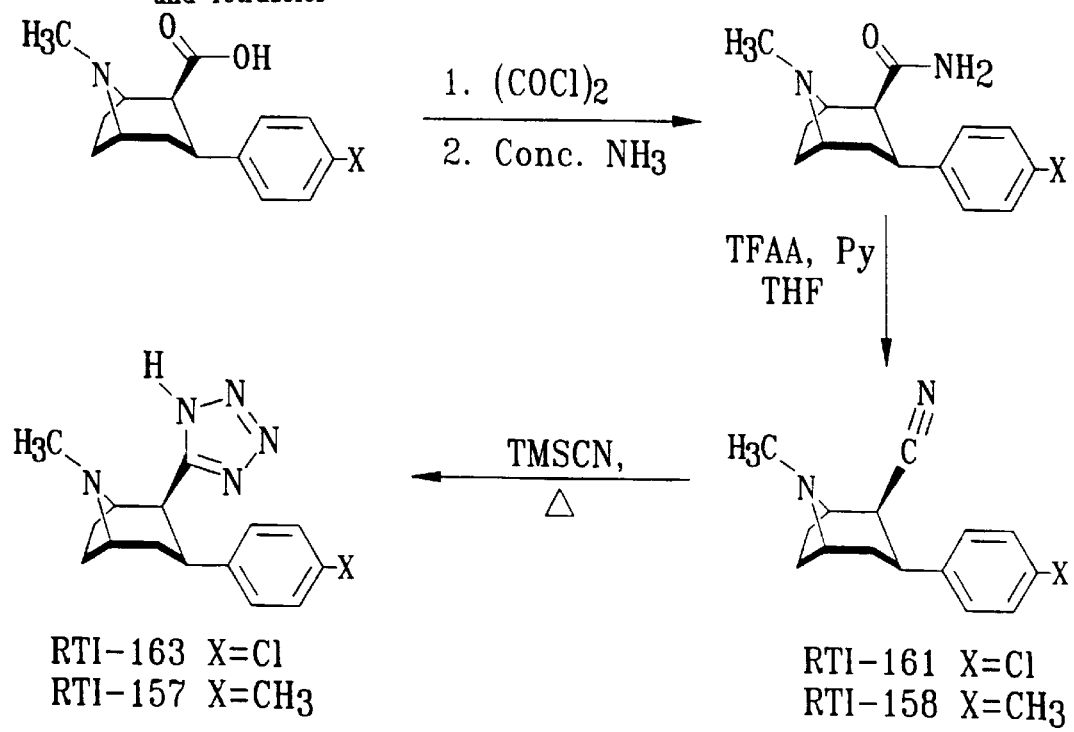
FIG. 2 depicts the scheme in which the carboxamide obtained from the tropane acid was treated to obtain nitrites and tetrazoles.

The known 3β-(substituted phenyl)-2β-tropane carboxylic acid (tropane acid) (Carroll et al., *J. Med. Chem.* 35:1813–1817 (1992)) served as the starting material for the synthesis of 2β-substituted tetrazoles, oxazoles, oxadiazoles, thiazoles, thiadiazoles and benzothiazole as shown in FIG. 1 and FIG. 2.

The tropane acid was refluxed with N-acetyl and benzoic hydrazide in phosphorous oxychloride to obtain the corresponding 5-substituted 1,3,4-oxadiazoles (Afanasiadi et al., *Chem. Heterocyclic Compd.* 397–400 (1995)). N-benzoyl hydrazide amide obtained by the reaction of the acid chloride of tropane acid with N-benzoic hydrazide was cyclized with Lawesson's reagent (El-Barbary et al., *Acta Chimica Scandinavica* 597–601 (1980)) in refluxing THF to the 5-substituted 1,3,4-thiadiazoles. The N-phenylacyl carboxamide obtained from tropane acid and 2-aminoacetophenone was cyclized by refluxing the amide in phosphorous oxychloride to obtain the required 5-substituted oxazoles (Carroll et al., *Med. Chem. Res.* 3:468 (1993)). Cyclization of the same amide with Lawesson's reagent (El-Barbary et al., 1980) in refluxing THF gave the 5-substituted thiazoles respectively. The benzothiazole was obtained without the cyclization step by the reaction of acid chloride obtained from the appropriate tropane acid with 2-aminothiophenol.

The previously reported carboxamide (Carroll et at., *J. Med. Chem.* 38:379–388, 1995) obtained from the tropane acid was dehydrated with trifluoroacetic acid and pyridine in THF to the nitrites (Campagna et al., *Tet. Letts.* 22:1813–1816 (1977)) as shown in FIG. 2. Cycloaddition of trimethylsilylazide to the nitrite afforded the corresponding tetrazoles (Saunders et al., *Med. Chem.* 33:1128–1138 (1990).

Figure 3:
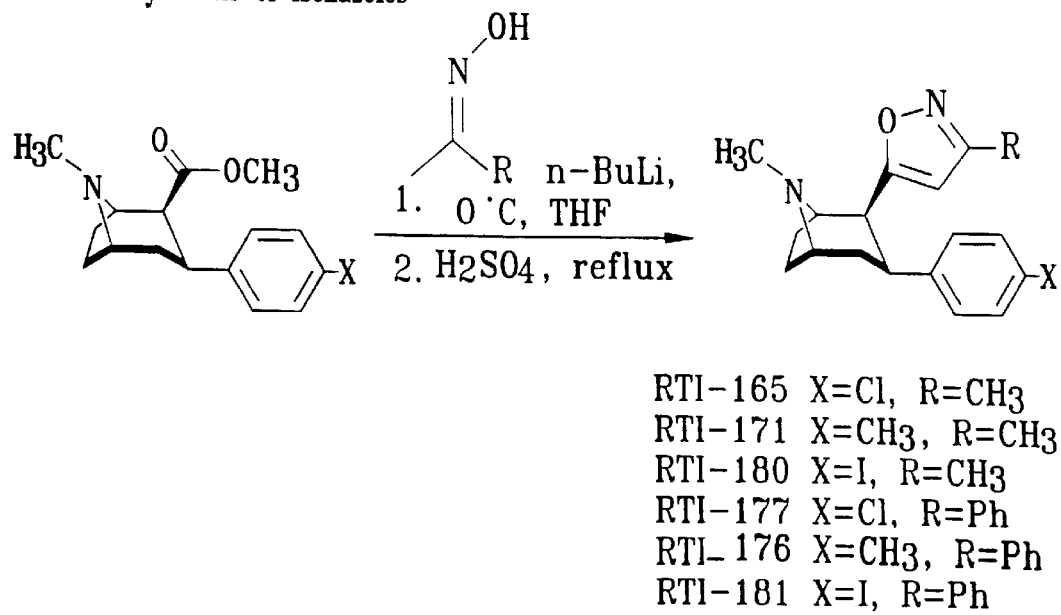
FIG. 3 depicts the scheme used to prepare 3-substituted isoxazoles.
Figure 4:
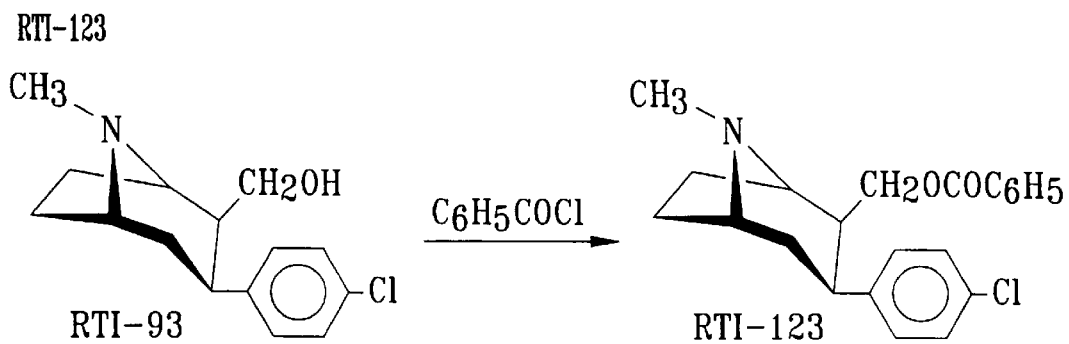
FIG. 4 depicts the scheme for converting RTI-93 to RTI-123.
Figure 5:
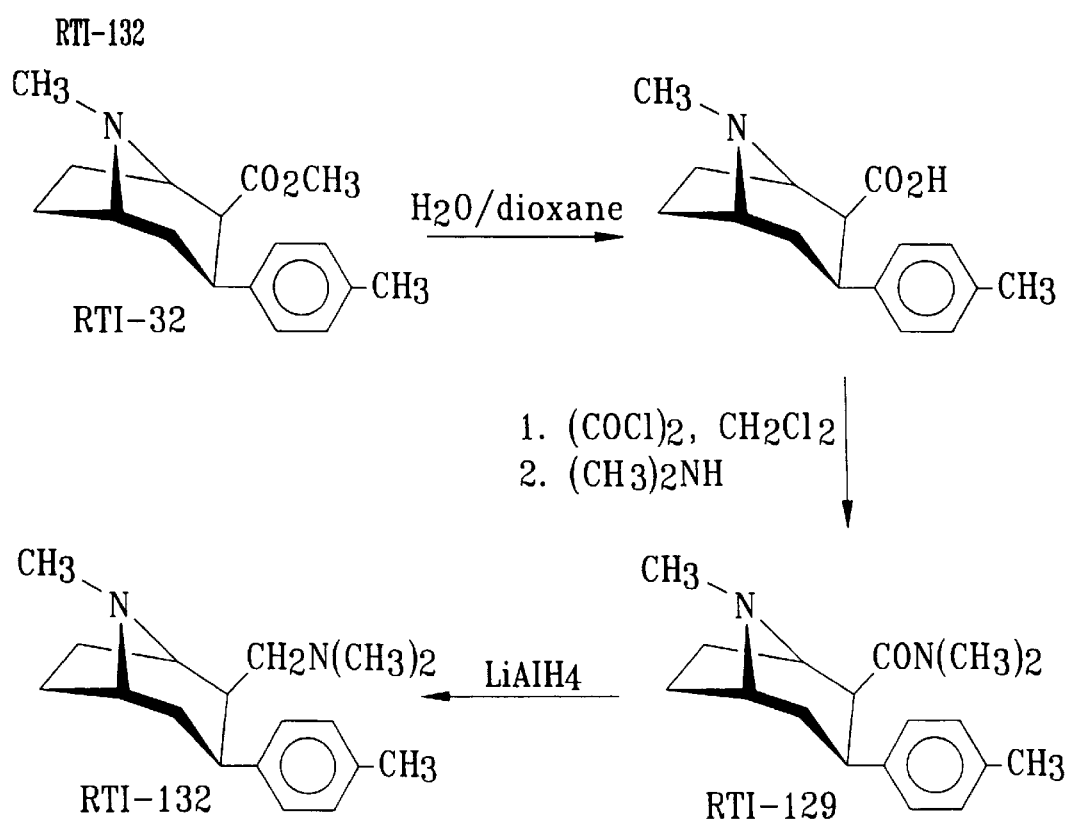
FIG. 5 depicts the scheme for converting a 3β-phenyltropane 2β-ester analog (RTI-32) to a 3β-phenyltropane 2β-amide analog (RTI-129) and a 3β-phenyltropane 2β-aminomethyl analog (RTI-132).
Figure 6:
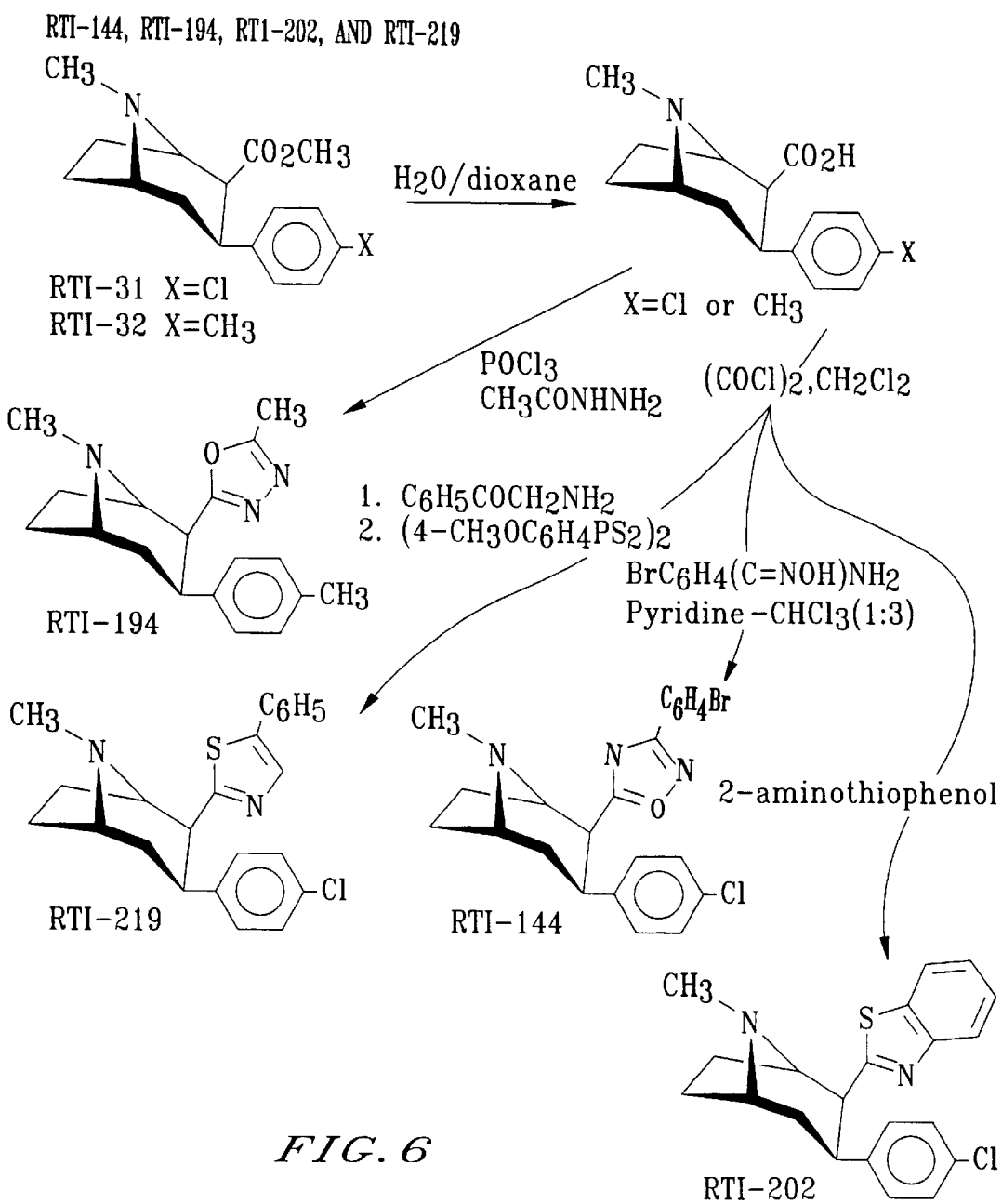
FIG. 6 depicts the scheme for converting a 3β-phenyltropane analog (RTI-31) or a 3β-phenyltropane 2β-ester analog (RTI-32) into a 3β-phenyltropane 2β-(3'-substituted-1,2,4-oxadiazol-5-yl) analog (RTI-144) or a 3β-phenyltropane 2β-heterocyclic analog (RTI-194, RTI-219, and RTI-202).
Figure 7:
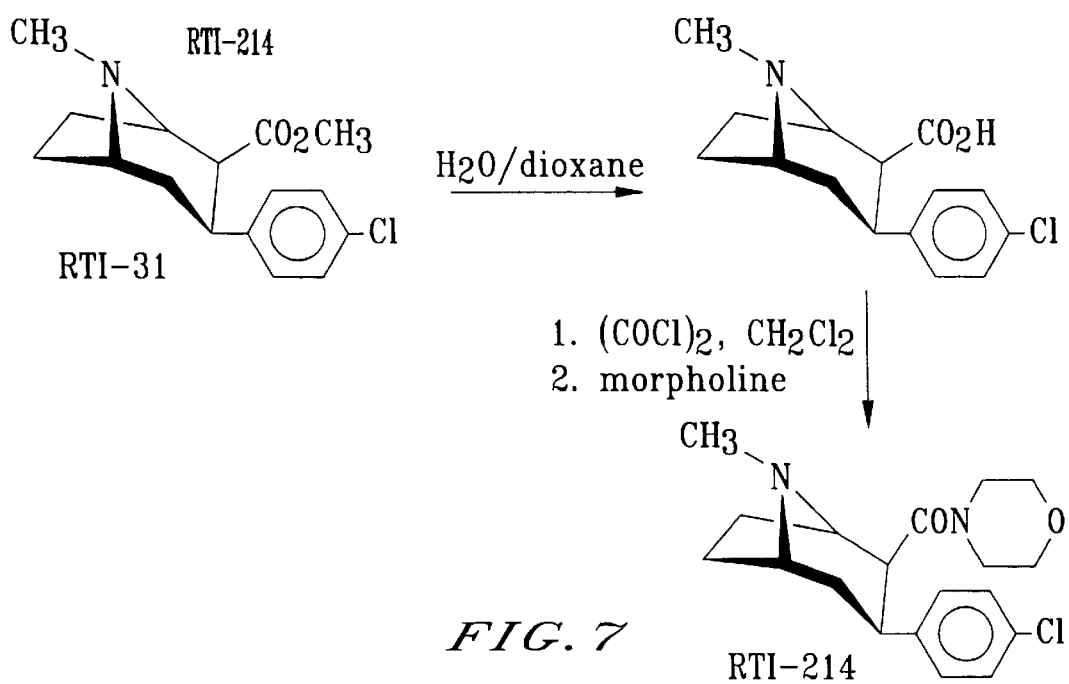
FIG. 7 depicts the scheme for converting a 3β-phenyltropane analog (RTI-31) into a 3β-phenyltropane 2β-amide analog (RTI-214).
Figure 8:
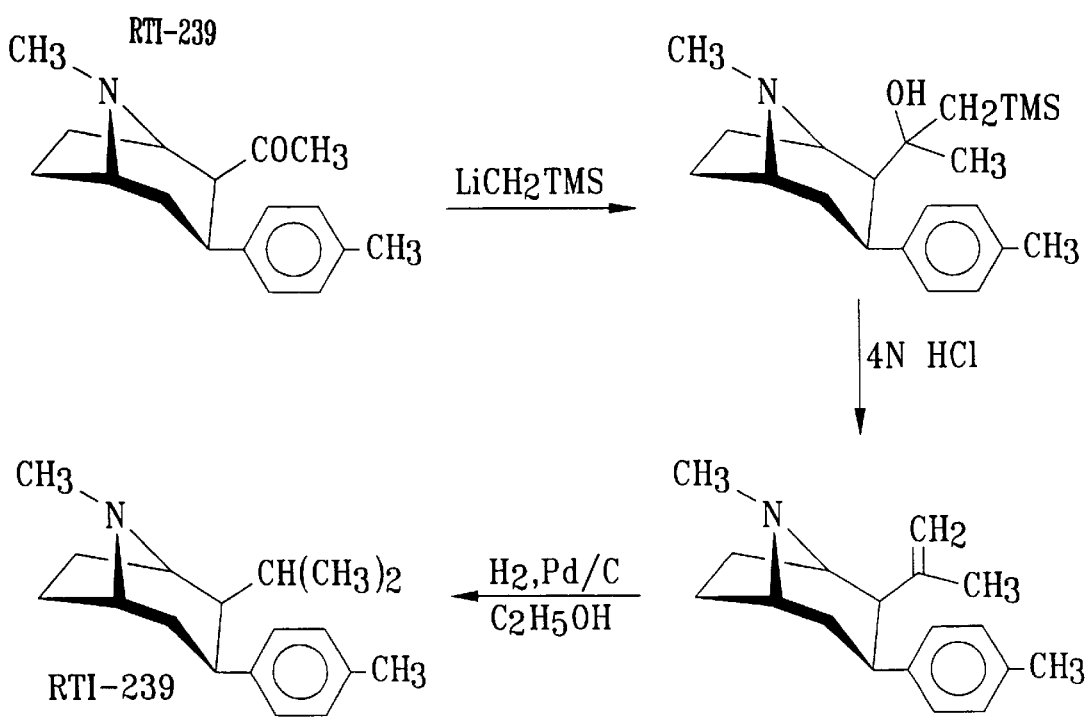
FIG. 8 depicts the scheme for making a 3β-phenyltropane 2β-alkyl analog (RTI-239).
Figure 9:
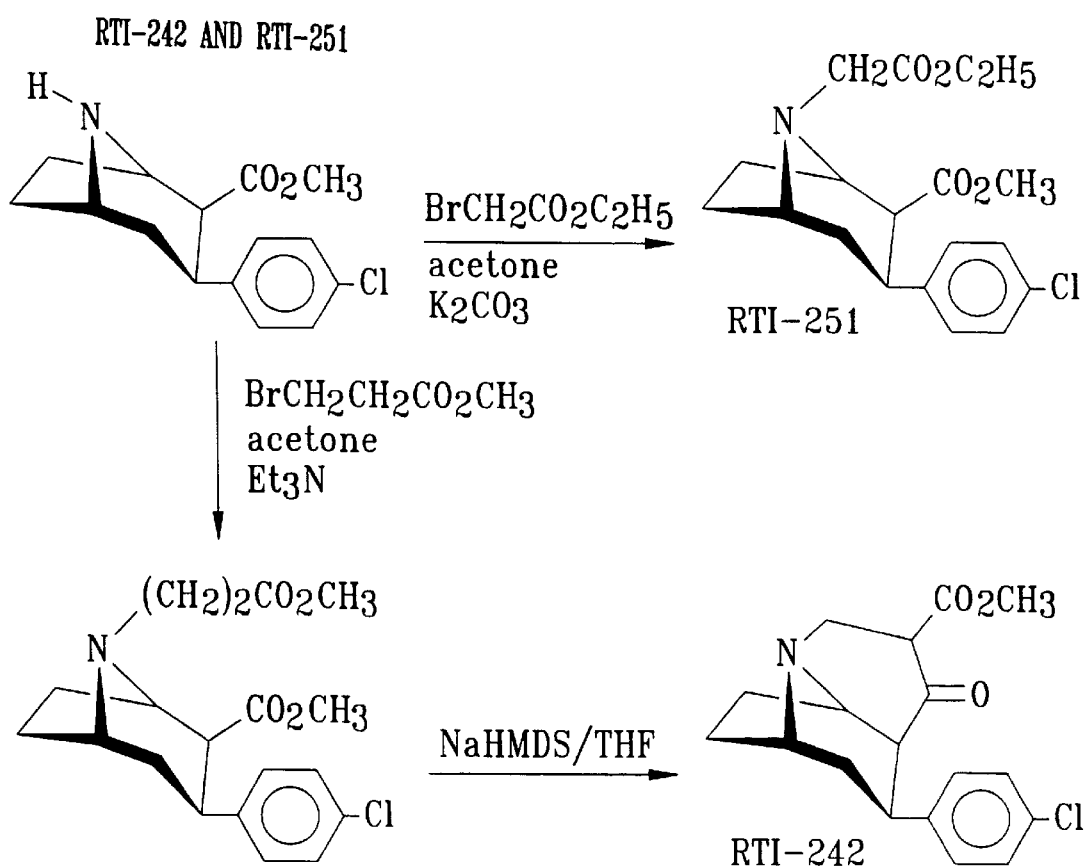
FIG. 9 depicts the scheme for making a 3β-phenyltropane analog (RTI-251) and an N,C2-fused 3β-phenyltropane analog (RTI-242).
Figure 10:
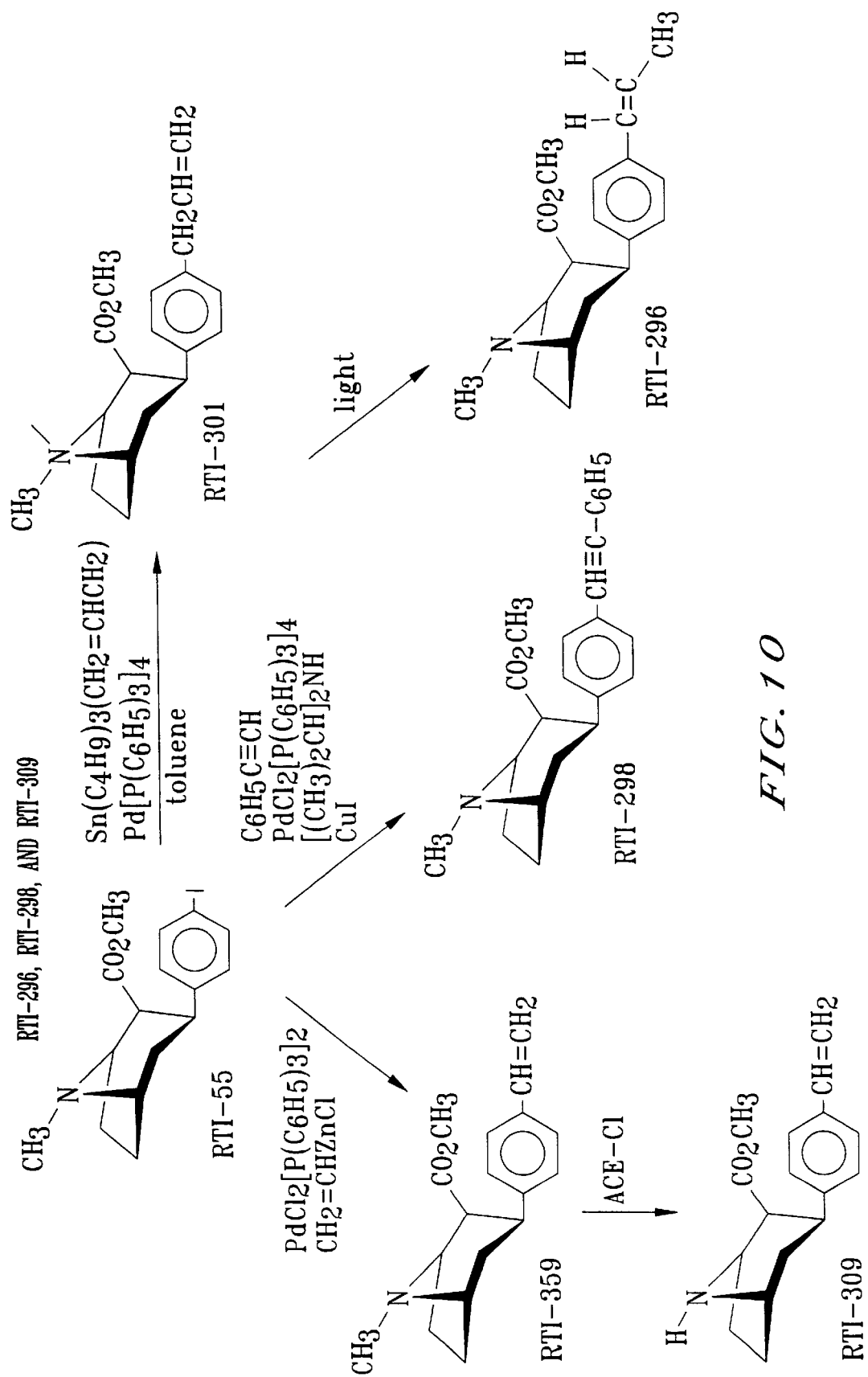
FIG. 10 depicts the scheme for making RTI compounds 296, 298 and 309.
Figure 11:
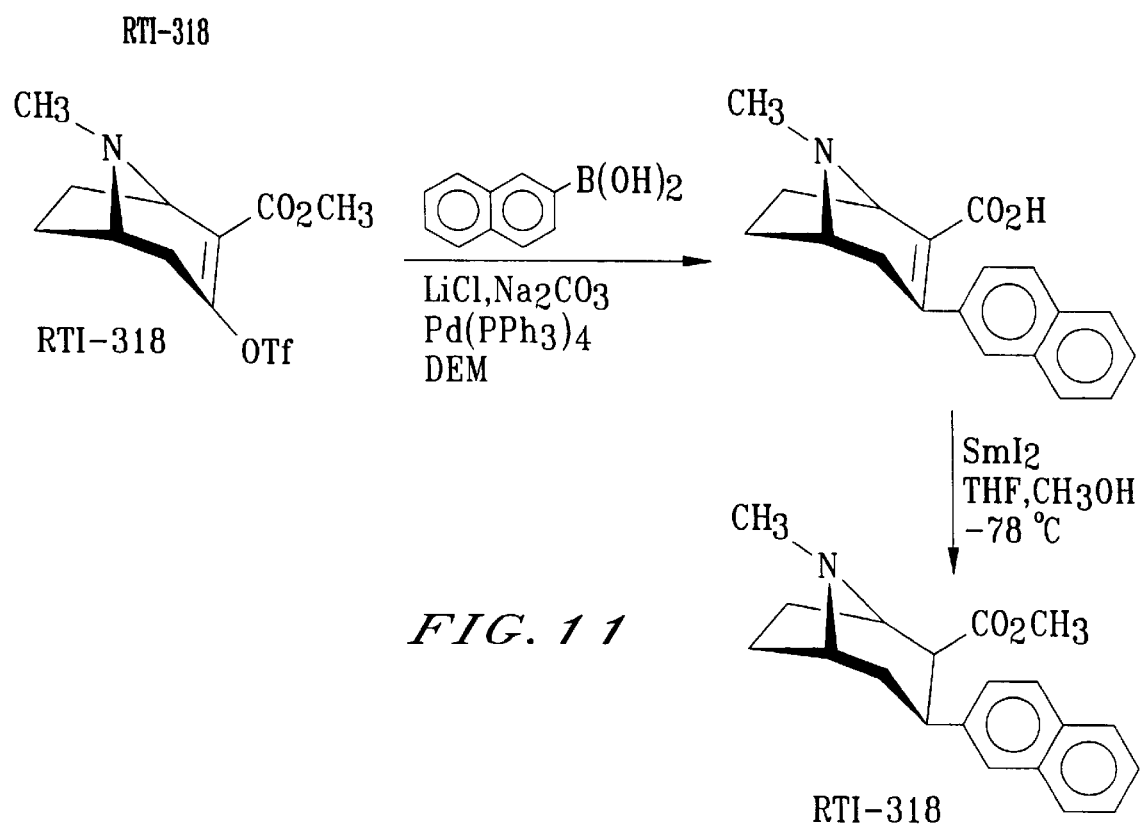
FIG. 11 depicts the scheme for making RTI-318.
Figure 12:
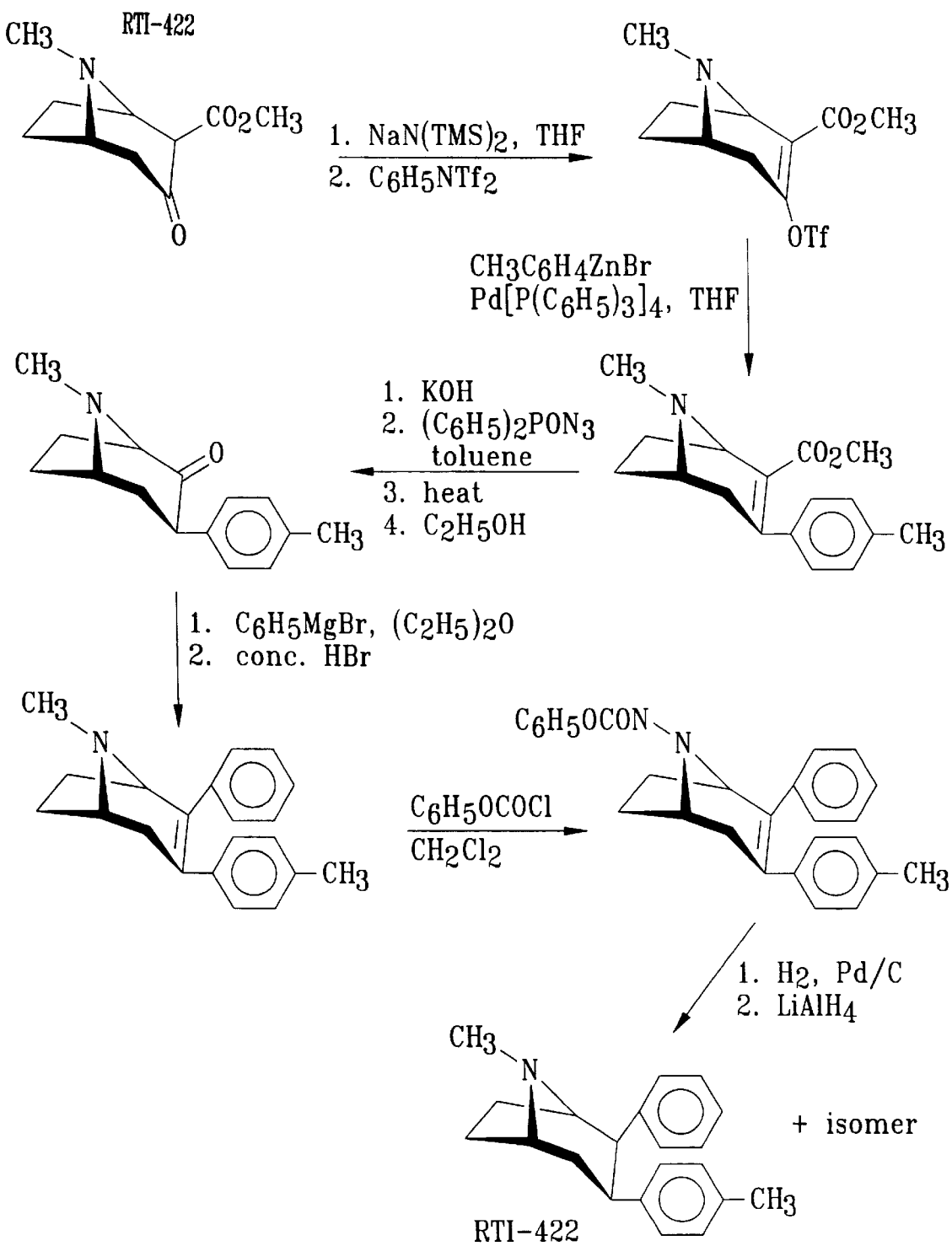
FIG. 12 depicts the scheme for making a 2β,3β-diphenyltropane analog (RTI-422).

FIG. 3 outlines the route used to prepare 3-substituted isoxazole. The known tropane compounds (Carroll et al., *J. Med. Chem.* 34:2719–2725 (1991)) were treated with dilithiated methyl or phenyl acetoneoximes, obtained by the treatment of acetone oxime, or acetophenoneoxime with n-BuLi at 0° C. The corresponding addition product was cyclized without isolation using sulfuric acid at reflux temperature to furnish the required isoxazoles (Saunders et al., 1990).

The therapeutic effects of the present cocaine analogs can be analyzed in various ways, many of which are well known to those of skill in the art. In particular, both in vitro and in vivo assay systems may be used for the screening of potential drugs which act as agonists or antagonists at cocaine receptors, or drugs which are effective to modulate neurotransmitter level or activity, in particular by binding to a transporter of that neurotransmitter.

The compounds of the invention may be prepared and labeled with any detectable moiety, in particular a radioactive element, and may then be introduced into a tissue or cellular sample. After the labeled material or its binding partner(s) has had an opportunity to react with sites within the sample, the location and concentration of binding of the compound may be examined by known techniques, which may vary with the nature of the label attached.

Illustrative in vitro assays for binding are described in Boja et al *Ann. NY Acad. Sci.* 654:282–291 (1992), which is incorporated herein by reference in its entirety. A particularly preferred in vitro assay involves the ability of a compound in question to displace the binding of a known labeled compound at binding sites in a tissue sample, isolated membranes or synaptosomes. Alternatively, the compounds may be analyzed by their ability to inhibit reuptake of a labelled neurotransmitter in a sample, in particular, in synaptosomes.

The compound or its binding partner(s) can also be labeled with any detectable moiety, but are preferably labelled with a radioactive element. The radioactive label can be detected by any of the currently available counting procedures, including the imaging procedures detailed in the disclosures of the parent applications. The preferred isotope may be selected from $^3$H, $^{11}$C, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, $^{123}$I, and $^{186}$Re.

As noted in the parent disclosures, the binding of the labelled compounds may be analyzed by various imaging techniques, including positron emission tomography (PET), single photon emission computed tomography (SPECT), autoradiogram, and the like. Such imaging techniques are useful for determining effective doses of new drug candidates. By performing in vivo competition studies, it is possible to use brain imaging studies to determine the oral doses of new drug candidates, which produce significant receptor occupancy in the brain. In vivo displacement studies which determine in vivo IC50's which in turn reflect doses that occupy receptors in vivo are described in Cline et al ((1992) *Synapse* 12:37–46). In addition to its uses in determining in vivo potency/occupancy, these same brain imaging methods can be used to determine rate of entry of compounds into the brain (Stathis et al (1995) *Psychopharmacology* 119:376–384) and duration of action (Volkow et al (1995) *Synapse* 19:206–211).

The binding of the compounds of the invention may be at any location where a receptor for a particular psychostimulant is present, and more specifically, any location where a dopamine or serotonin transporter is present. Such locations are in general any area comprising a part of the dopamine or serotonin pathway, in particular at or near synapses. Examples of locations known to be associated with dopamine transport include the cerebral cortex, hypothalamus, substantia nigra, nucleus accumbens, arcuate nucleus, anterior periventricular nuclei, median eminence and amygdala. Examples of locations known to be associated with serotonin include the striatum, cerebral cortex, hypothalamus, Raphe nuclei, pre-optic area and suprachiasmatic nucleus.

By "psychostimulant" is meant compounds whose abuse is dependent upon mesolimbic and mesocortical dopaminergic pathways. In particular, psychostimulant relates to cocaine and amphetamine. However, the compounds of the invention may also be used to treat abuse of compounds not traditionally classified as "psychostimulants," but which act by altering dopamine or serotonin systems in brain. Such abused compounds include ethanol and nicotine.

For in vivo studies, the compounds of the invention may be prepared in pharmaceutical compositions, with a suitable carrier and at a strength effective for administration by various means to a patient experiencing an adverse medical condition associated with cocaine receptor binding or neurotransmitter release and reuptake, for the treatment thereof. The action of the compounds may be analyzed by the imaging methods noted above, and also by behavioral studies. In particular, the pharmaceutical effects of the compounds of the invention may be reflected in locomotor activity, including the induction of ipsilateral rotation, stereotyped sniffing and the "swim test", in schedule-controlled operant behavior (i.e., response for food or shock termination) or drug self-administration. In general, maximal behavioral effects are seen at near complete occupancy of transporter sites. Such protocols are described in Boja et al (1992), Balster et al *Drug and Alcohol Dependence* 29:145–151 (1991), Cline et al *Pharm. Exp. Ther.* 260:1174–1179 (1992), and Cline et al *Behavioral Pharmacology* 3:113–116 (1992), which are hereby incorporated herein by reference in their entireties.

A variety of administration techniques may be utilized, among them oral or parenteral techniques such as subcutaneous, intravenous, intraperitoneal, intracerebral and intracerebroventricular injections, catheterizations and the like. Average quantities of the compounds may vary in accordance with the binding properties of the compound (i.e., affinity, onset and duration of binding) and in particular should be based upon the recommendations and prescription of a qualified physician or veterinarian.

The compounds of the invention preferably have a long duration of action, which is important to facilitate dosing schedules. In rats, the present compounds have a 7–10 fold longer duration of action than cocaine (Fleckenstein et al, "Highly potent cocaine analogs cause long-lasting increases in locomotor activity," *Eur. J. Pharmacol.,* which is incorporated herein by reference in its entirety). In addition, the present compounds also preferably have a slow rate of entry into the brain, which is important in decreasing the potential for abuse (Stathis et al, supra, which is incorporated herein by reference in its entirety). The present compounds enter the brain more slowly than cocaine.

The therapeutic compositions useful in practicing the therapeutic methods of this invention may include, in admixture, a pharmaceutically acceptable excipient (carrier) and one or more of the compounds of the invention, as described herein as an active ingredient.

The preparation of therapeutic compositions which contain such neuroactive compounds as active ingredients is well understood in the art. Such compositions may be prepared for oral adminstration, or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, and pH buffering agents which enhance the effectiveness of the active ingredient. The compounds of the invention can be formulated into the therapeutic composition as neutralized pharmaceutically acceptable salt forms.

The therapeutic compositions are conventionally administered orally, by unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, the presence of other agonists and antagonists in the subject's system, and degree of binding or inhibition of binding desired. Precise amounts of active ingredient required to be administered depend on the judgment of the practitioner and are peculiar to each individual. However, suitable dosages may range from about 0.01 to about 1000, preferably about 0.25 to about 500, and more preferably 10 to 50 milligrams of active ingredient per kilogram body weight of individual per day and depend on the route of administration. However, the exact dosage must be determined by factoring in rate of degradation in the stomach, absorption from the stomach, other medications administered, etc. Suitable regimes for administration are also variable, but are typified by an initial administration followed by repeated doses at one or more hour intervals by a subsequent injection or other administration. Alternatively, continuous intravenous infusion sufficient to maintain appropriate concentrations in the blood are contemplated.

The compounds of the present invention may be administered for their activities as surrogate agonist medications for cocaine, nicotine, alcohol, amphetamine and other psychostimulant abuse. Because of their favorable binding characteristics to transporters of neurotransmitters, they may be used for inhibiting the uptake of dopamine, norepinephrine, serotonin and other monoamines. The compounds of the present invention may find use as antipsychotics, antidepressants, local anesthetics, anti-Parkinsonian agents, anti-obesity drugs, drugs useful in the treatment of bipolar disorder, eating disorders, obesity, attention deficit disorder, panic attacks and disorder, obsessive-compulsive disorder, sexual dysfunction, as anticholinergic agents and as sigma receptor drugs.

The compounds of the invention may also be useful in treating neurodegenerative disorders, in particular for treating Parkinson's Disease, but also may be useful in the treatment of cocaine, nicotine and alcohol addiction.

The preferred compounds of the present invention are derived from the series of compounds designated RTI-4229. The physical properties of some of these compounds are given in Table I.

TABLE 1

Physical Properties of 2β-substituted Heterocyclic Analogs of 3β-(4-Substituted-phenyl) Tropane and Cocaine

| Code Name | Molecular Formulae[a] | mp° C. | [α]D (c) MeOH | Yield % |
|---|---|---|---|---|
| RTI-188 | $C_{22}H_{23}Cl_2N_3O^e$ | 160–162 | +84.59 (0.36) | 42 |
| RTI-195 | $C_{23}H_{26}CN_3O^e$ | 175–178 | +97.22 (0.25) | 40 |
| RTI-194 | $C_{18}H24_{CN}3_0{}^d$ | 146 (dec) | −43.05 (0.15) | 58 |
| RTI-200 | $C_{22}H_{23}Cl_2N_3S^e$ | 165–170 | −42.81 (0.16) | 58 |
| RTI-199 | $C_{23}H_{26}CN_3S^d$ | 180–185 | −33.50 (0.20) | 58 |
| RTI-189 | $C_{27}H_{29}CN_2O_7{}^{b,e}$ | 126 (dec) | +101.43 (0.21) | 49 |
| RTI-178 | $C_{29}H_{32}N_3O_7{}^{b,f}$ | 175–181 | −104.04 (0.60) | 72 |
| RTI-219 | $C_{23}H_{24}CN_2S^f$ | 228–230 | +27.43 (0.11) | 30 |
| RTI-202 | $C_{21}H_{22}Cl_2N_2S^c$ | 140–150 (dec) | −172.49 (0.28) | 41 |
| RTI-161 | $C_{15}H_{18}Cl_2N_2{}^e$ | >220 (dec) | −71.00 (0.50) | 77 |
| RTI-158 | $C_{16}H_{21}CN_2$ | 270 (dec) | −76.40 (0.50) | 67 |
| RTI-163 | $C_{15}H_{18}CN_5{}^e$ | 296–300 | −124.94 (0.39) | 33 |
| RTI-157 | $C_{16}H_{23}Cl_2N_5{}^c$ | <212 (dec) | −110.97 (0.16) | 88 |
| RTI-165 | $C_{18}H_{22}Cl_2N_2O$ | 235 (dec) | −102.89 (0.46) | 46 |
| RTI-171 | $C_{19}H_{25}CN_2O$ | 277 | −107.28 (0.71) | 62 |
| RTI-180 | $C_{18}H_{22}CN_2O^c$ | <235 (dec) | −94.57 (0.39) | 49 |
| RTI-177 | $C_{23}H_{24}Cl_2N_2O^c$ | 287 | −97.50 (0.28) | 50 |
| RTI-176 | $C_{24}H_{27}CN_2O$ | 270–295 (dec) | −102.22 (0.68) | 77 |

TABLE 1-continued

Physical Properties of 2β-substituted Heterocyclic
Analogs of 3β-(4-Substituted-phenyl) Tropane and Cocaine

| Code Name | Molecular Formulae[a] | mp° C. | [α]D (c) MeOH | Yield % |
|---|---|---|---|---|
| RTI-181 | $C_{23}H24_{CN_2}O_3$[d] | <2679 (dec) | −91.11 (0.43) | 56 |
| RTI-184 | $C_{19}H_{23}CN_2O_3$[d] | 117–121 | −53.60 (0.25) | 82 |
| RTI-185 | $C_{24}H_{25}CN_2O_3$ | 205 | −56.71 (0.43) | 68 |

[a]HC1 Salt;
[b]Tartrate Salt
[c]0.25 mol water;
[d]0.5 mol water;
[e]0.75 mol water;
[f]1 mol water.

Many of the preferred compounds of the invention fall within the broad class of compounds described by the formula:

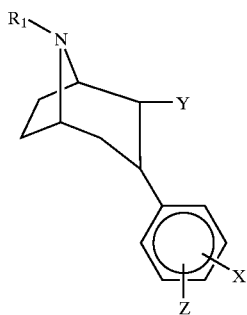

wherein $Y=CH_2R_3$, $CO_2R_2$, $CONRR^1$,

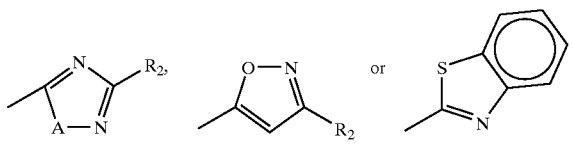

$R_1$=hydrogen, $C_{1-5}$ alkyl,
$R_2$=hydrogen, $C_{1-6}$ alkyl, $C_{3-8}$ cycloalkyl, $C_{1-4}$ alkoxy, $C_{1-6}$alkynyl, halogen, amine, $CH_2C_6H_5$, $(CH_2)_2C_6H_5$, $(CH_2)_3C_6H_5$ or

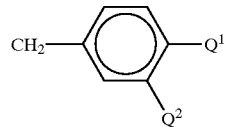

$R_3$=OH, hydrogen, $C_{1-6}$ alkyl, $C_{3-8}$ cycloalkyl, $C_{1-4}$ alkoxy, Cl, Br, I, CN, $NH_2$, $NHC_{1-6}$ alkyl, $NC_{1-6}$ alkyl, $OCOC_{1-6}$ alkyl, OCOC alkylaryl,
A=S, O or N
X=H, $C_{1-6}$ alkyl, $C_{3-8}$ cycloalkyl, $C_{1-4}$ alkoxy, $C_{1-6}$ alkynyl, halogen, amino, acylamido, $C_2H_5$, $CH_2CH_3CH_3$, $CH(CH_3)_{21}$ Z=H, I, Br, Cl, F, CN, $CF_3$, $NO_2$, $N_3$, $OR_1$, $CONH_2$, $CO_2R$, $C_{1-6}$ alkyl, $NR_4R_5$, $NHCOR_5$, $NHCO_2R_6$, and $Q^1$ and $Q^2$ may be the same or different and =H, $OCH_3$, or Cl,
wherein $R_4$–$R_6$ are each $C_{1-6}$ alkyl, R and $R^1$ are independently H, $C_{1-6}$ alkyl, $C_{1-6}$ alkene, $C_{1-6}$ alkyne, phenyl, phenyl substituted with 1–3 of $C_{1-6}$ alkyl, alkene, alkyl or alkoxy, $C_{1-6}$ alkoxy, phenoxy, amine, amine substituted with 1–2 of $C_{1-6}$ alkyl, alkene, alkyne, alkoxy or phenyl or phenoxy or R and $R^1$ may combine to form heterocyclic structure including pyrrolidinyl, piperidinyl and morpholino moieties, unsubstituted or substituted with 1–2 $C_{1-6}$ alkyl, alkene, alkyne or alkoxy groups.

The present inventors have surprisingly found that certain of the RTI-4229 series of compounds are particularly potent pharmaceutical agents in accordance with the present invention.

Preferred compounds of the RTI-4229 series include the following: RTI-4229-31, 32, 51, 55, 83, 96, 97, 98, 101, 105, 108, 110, 111, 112, 116, 121, 122, 123, 127, 132, 139, 140, 142, 145, 146, 147, 150, 153, 173, 178, 188, 189, 190, 191, 193, 195, 199, 200, 203, 204, 205, 206, 214, 219, 230, 239, 240, 241, 242, 243, 251, 252, 274, 277, 278, 279, 280, 281, 282, 283, 286, 287, 296, 304, 305, 307, 309, 318, 330 and 422. The chemical structures of these compounds, along with their $IC_{50}$ values for inhibition of radioligand binding are given below. DA is dopamine, 5-HT is 5-hydroxytryptamine (serotonin), and NE is norepinephrine, DA=[$^3$H]WIN 35,428; 5-HT=[$^3$H] paroxetine and $NE_N$= [$^3$H] nisoxetine:

RTI-4229-31
DA  1.12 ± 0.1
5-HT 44.5 ± 1.34
$NE_N$ 37 ± 2.1

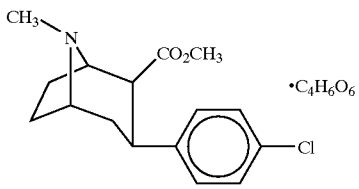

RTI-4229-32
DA  1.71 ± 0.31
5-HT 240 ± 27
$NE_N$ 60 ± 0.53

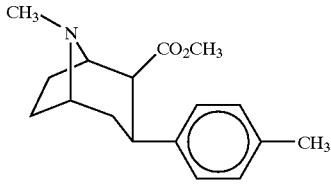

RTI-4229-51

-continued
DA  1.69 ± 0.23
5-HT 240 ± 0.24
$NE_N$  37.4 ± 5.2
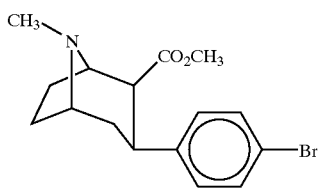
RTI-4229-55
DA  1.26 ± 0.04
5-HT 4.21 ± 0.34
$NE_N$  36 ± 3
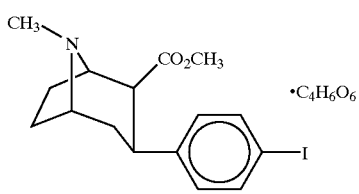
•$C_4H_6O_6$
RTI-4229-83
DA  55 ± 2
5-HT 28.4 ± 3.83
$NE_N$  4.027.87 ± 380.70
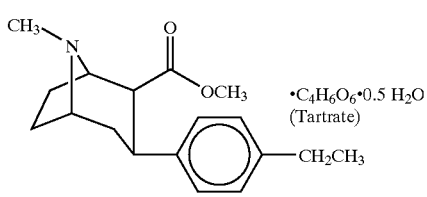
•$C_4H_6O_6$•0.5 $H_2O$
(Tartrate)
RTI-4229-96
DA  2.95 ± 0.58
5-HT 76 ± 2.8
$NE_N$  520 ± 10.4
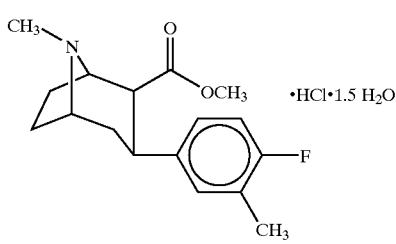
•HCl•1.5 $H_2O$
RTI-4229-97
DA  3.91 ± 0.59
5-HT 181 ± 14
$NE_N$  282 ± 30
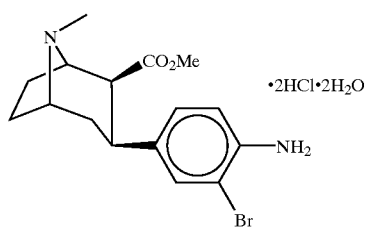
•2HCl•2$H_2O$
RTI-4229-98
DA  0.69 ± 0.2
5-HT 0.36 ± 0.047
$NE_N$  10.97 ± 0.88
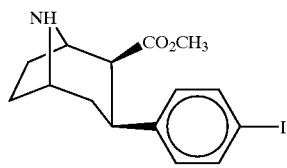
RTI-4229-101
DA  2.2 ± 0.19
5-HT 26 ± 3.2
$NE_N$  ±
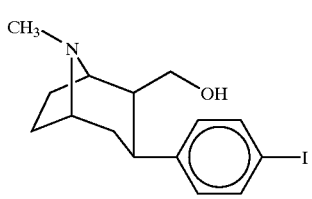
RTI-4229-105

-continued
DA  1.60 ± 0.05
5-HT 143 ± 25
$NE_N$  127.2 ± 5.9
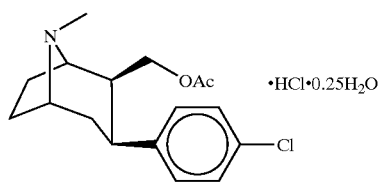
RTI-4229-108
DA  2.64 ± 0.31
5-HT 98 ± 8.7
$NE_N$  129.3 ± 15
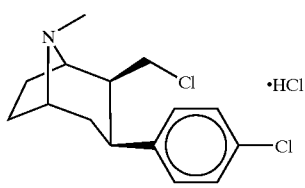
RTI-4229-110
DA  0.62 ± 0.09
5-HT 4.13 ± 0.62
$NE_N$  5.45 ± 0.21
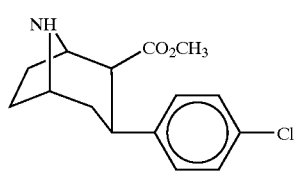
RTI-4229-111
DA  0.79 ± 0.08
5-HT 3.13 ± 0.36
$NE_N$  17.96 ± 0.85
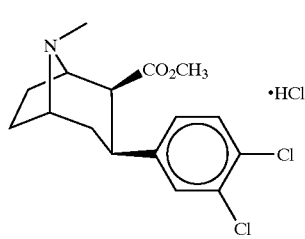
RTI-4229-112
DA  0.82 ± 0.05
5-HT 10.5 ± 0.41
$NE_N$  36.2 ± 1.02
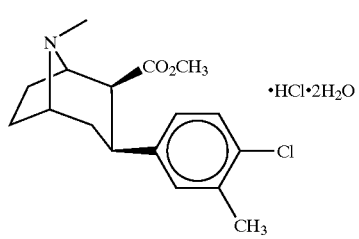
RTI-4229-116
DA  33 ± 3.9
5-HT 1,227 ± 176
$NE_N$  967.55 ± 26.25
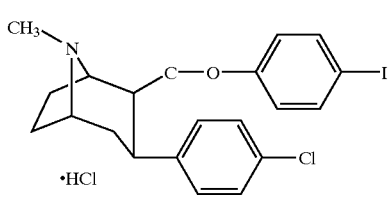
RTI-4229-121
DA  0.43 ± 0.05
5-HT 55.84 ± 6.53
$NE_N$  285 ± 7.6
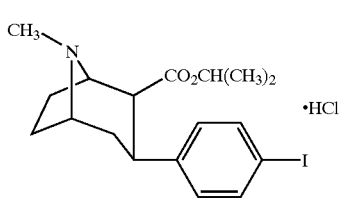
RTI-4229-122

-continued
DA  1.50 ± 0.35
5-HT 184.38 ± 21.91
$NE_N$ 3,791 ± 149
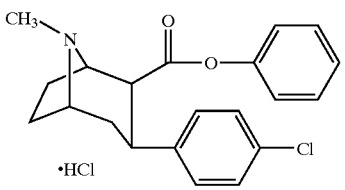
RTI-4229-123
DA  1.78
5-HT 3.53
$NE_N$ 393
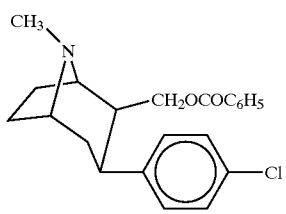
RTI-4229-127
DA  19 ± 1
5-HT 4,499 ± 557
$NE_N$ 3,444 ± 44
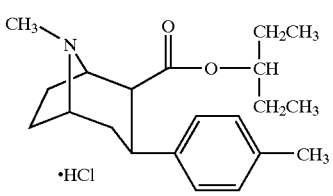
RTI-4229-132
DA  3.48 ± 0.11
5-HT 208 ± 18
$NE_N$ 137.3 ± 10.5
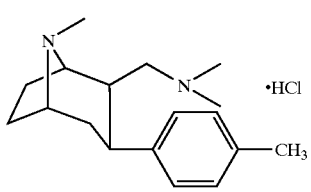
RTI-4229-139
DA  1.67 ± 0.13
5-HT 85 ± 9.3
$NE_N$ 56.9 ± 2.6
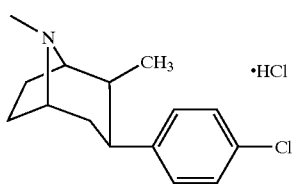
RTI-4229-140
DA  101 ± 16
5-HT 5,701 ± 721
$NE_N$ 2,076 ± 285
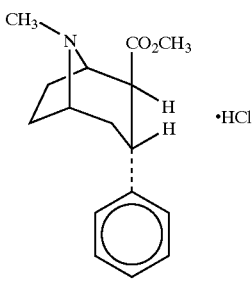
RTI-4229-142
DA  4.39 ± 0.20
5-HT 68.59 ± 2.02
$NE_N$ 18.78 ± 0.68
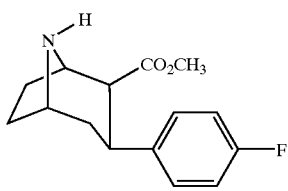

-continued
RTI-4229-145
DA 9.60 ± 0.42
5-HT 2,932 ± 181
$NE_N$ 1,478 ± 96
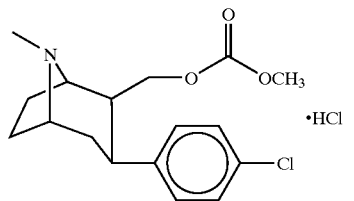
·HCl
RTI-4229-146
DA 2.05 ± 0.23
5-HT 98 ± 10
$NE_N$ 144 ± 3
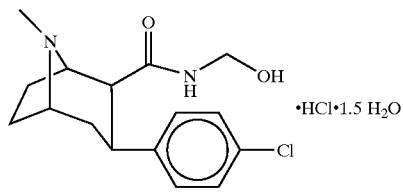
·HCl·1.5 $H_2O$
RTI-4229-147
DA 1.38 ± 0.03
5-HT 12,393.99 ± 1207.03
$NE_N$ 3,949 ± 72
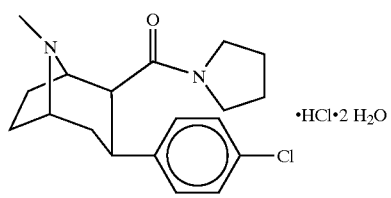
·HCl·2 $H_2O$
RTI-4229-150
DA 3.74 ± 0.52
5-HT 2,019 ± 133
$NE_N$ 4,738 ± 322
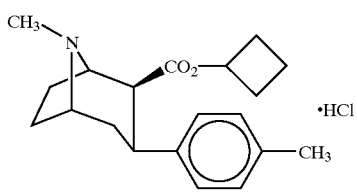
·HCl
RTI-4229-153
DA 1.06 ± 0.12
5-HT 3.59 ± 0.27
$NE_N$ 132 ± 5
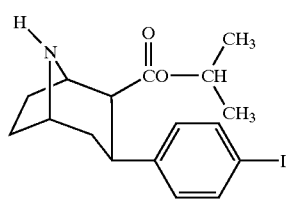
RTI-4229-173
DA 49.9 ± 7.3
5-HT 8.13 ± 0.30
$NE_N$ 122 ± 12
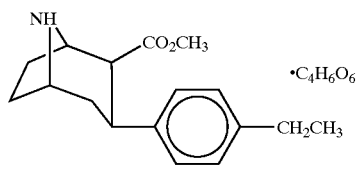
·$C_4H_6O_6$
RTI-4229-178
DA 35.4 ± 1.74
5-HT 1.698.77 ± 166.68
$NE_N$ 677 ± 67.5
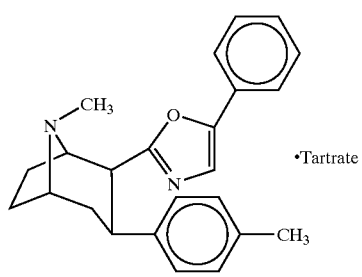
·Tartrate -continued
RTI-4229-188
DA 12.56 ± 1.03
5-HT 3,303.76 ± 195.85
NE$_N$ 929 ± 88.1
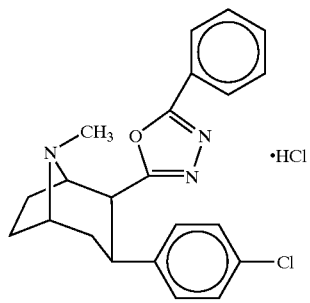
RTI-4229-189
DA 19.71 ± 1.98
5-HT 1,116.18 ± 107.148
NE$_N$ 496 ± 42.1
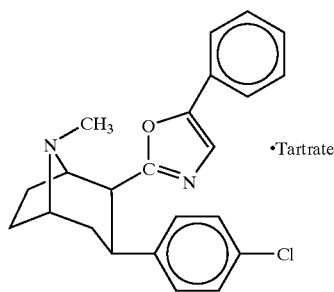
RTI-4229-190
DA 0.96 ± 0.10
5-HT 168 ± 1.8
NE$_N$ 235 ± 8.39
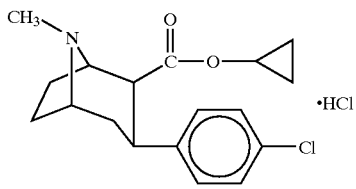
RTI-4229-191
DA 0.61 ± 0.08
5-HT 15.5 ± 0.72
NE$_N$ 101.7 ± 10.5
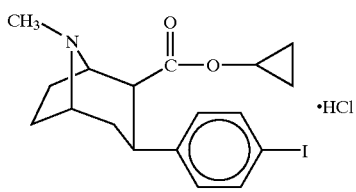
RTI-4229-193
DA 1.68 ± 0.14
5-HT 1,066.38 ± 109.12
NE$_N$ 544 ± 27.7
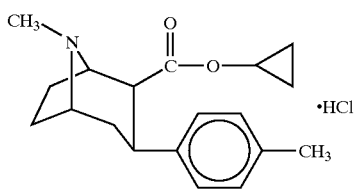
RTI-4229-195

-continued
DA  47.48 ± 4.76
5-HT  22,310.9 ± 822.83
NE$_N$  1,310 ± 36.7
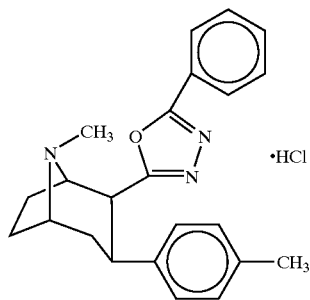
RTI-4229-199
DA  35.88 ± 3.40
5-HT  51,459.7 ± 4.513.10
NE$_N$  24,320.8 ± 3.822.61
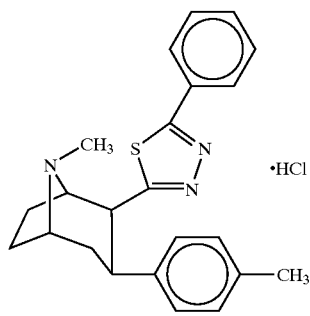
RTI-4229-200
DA  15.29 ± 2.43
5-HT  18,416.5 ± 1.508.79
NE$_N$  4,142.08 ± 466.07
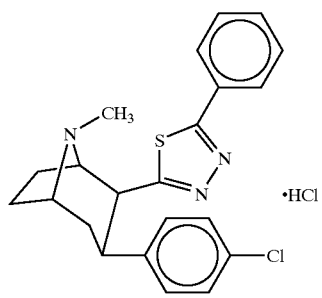
RTI-4229-203
DA  9.37 ± 0.52
5-HT  2,153.39 ± 143.18
NE$_N$  2,743.73 ± 140.92
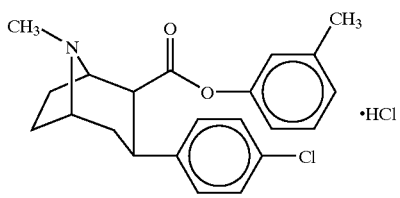
RTI-4229-204
DA  3.91 ± 0.23
5-HT  3,772.17 ± 383.64
NE$_N$  4,782.70 ± 487.10
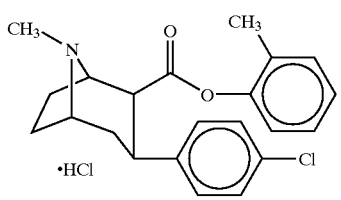
RTI-4229-205

-continued
DA 8.19 ± 0.90
5-HT 5,237.30 ± 453.397
NE$_N$ 2,136.62 ± 208.52
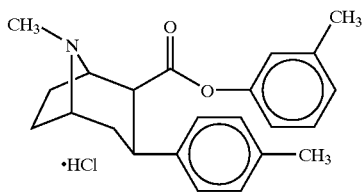
RTI-4229-206
DA 27.38 ± 1.47
5-HT 1,203.39 ± 41.79
NE$_N$ 1,277.60 ± 117.68
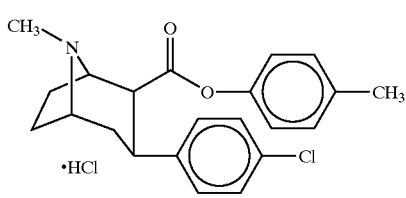
RTI-4229-214
DA 2.90
5-HT 88,800
NE$_N$ 8550
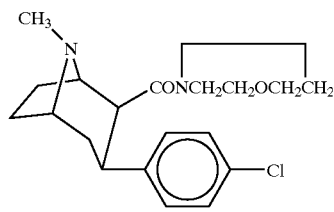
RTI-4229-219
DA 5.71 ± 0.36
5-HT 10.341 5 ± 76.11
NE$_N$ 8,563 ± 824
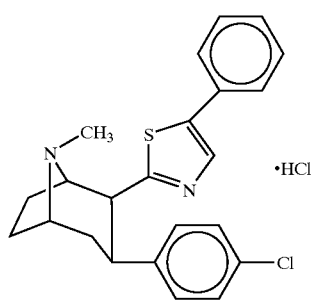
RTI-4229-230
DA 1.26 ± 0.17
5-HT 57.41 ± 5.04
NE$_N$ 141 ± 16.1
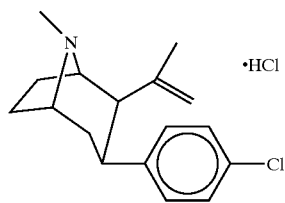
RTI-4229-239
DA 0.61 ± 0.07
5-HT 114.3 ± 3.69
NE$_N$ 35.6 ± 2.57
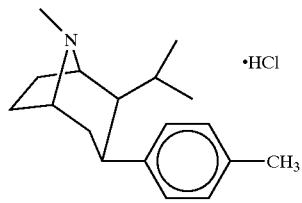
RTI-4229-240

-continued
DA 1.38 ± 0.03
5-HT 38.4 ± 2.31
NE$_N$ 84.5 ± 3.09
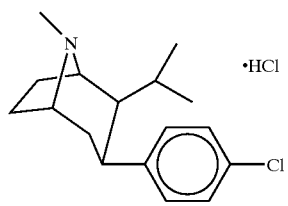
RTI-4229-241
DA 1.02 ± 0.06
5-HT 618.5 ± 28
NE$_N$ 124 ± 3.56
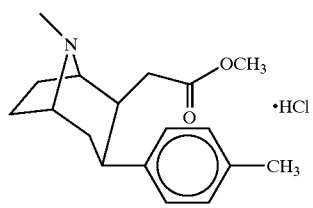
RTI-4229-242
DA 7.57 ± 0.31
5-HT 226.54 ± 27.37
NE$_N$ 510.1 ± 51.4
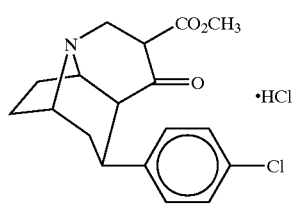
RTI-4229-243
DA 129 ± 19.6
5-HT 155.93 ± 15.27
NE$_N$ 540 ±
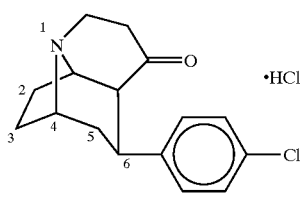
RTI-4229-251
DA 1.93 ± 0.14
5-HT 10.1 ± 1.1
NE$_N$ 114 ± 13.1
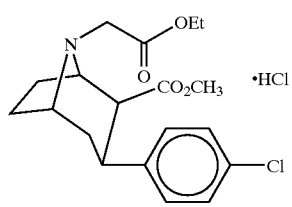
RTI-4229-252
DA 2.56 ± 0.22
5-HT 35.2 ± 2.45
NE$_N$ 124.6 ± 8.3
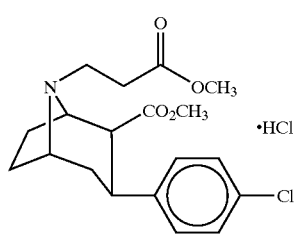
RTI-4229-274

-continued
DA    3.96 ± 0.2
5-HT  5.62 ± 0.2
$NE_N$  14.4 ± 1.3
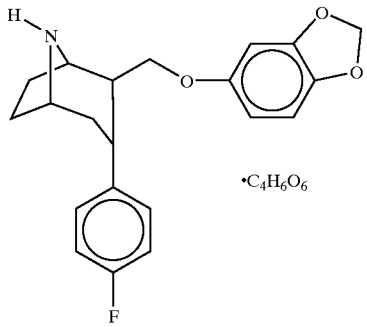
RTI-4229-277
DA    5.94 ± 0.61
5-HT  2,909.71 ± 255.41
$NE_N$  5,695.38 ± 214.72
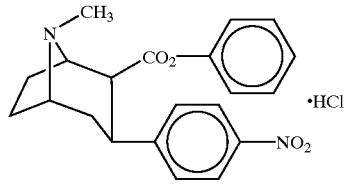
RTI-4229-278
DA    8.14 ± 0.73
5-HT  2,146.50 ± 138.71
$NE_N$  4,095.01 ± 413.45
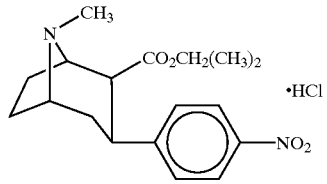
RTI-4229-279
DA    5.96 ± 0.48
5-HT  1.06 ± 0.10
$NE_N$  74.3 ± 3.8
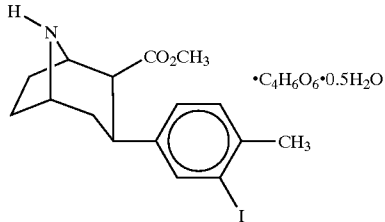
RTI-4229-280
DA    3.12 ± 0.39
5-HT  6.81 ± 0.41
$NE_N$  484.13 ± 51.6
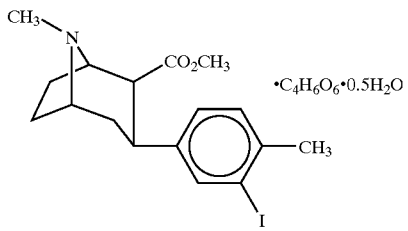
RTI-4229-281
BIH-141-7
DA    2.37 ± 0.28
5-HT  15.69 ± 1.5
$NE_N$  820.5 ± 45.8
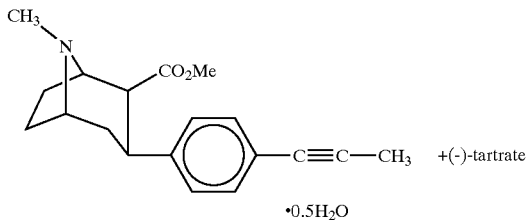
RTI-4229-282
BIH-141-2

-continued
DA 68.53 ± 7.08
5-HT 70.38 ± 4.13
$NE_N$ 3921.58 ± 130
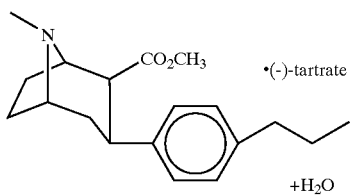
•(-)-tartrate
+$H_2O$
RTI-4229-283
BIH-141-2
DA 14.35 ± 0.3
5-HT 3.13 ± 0.16
$NE_N$ 3125 ± 333
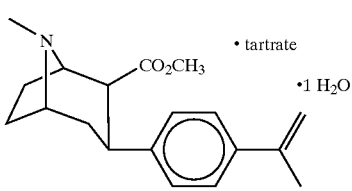
• tartrate
•1 $H_2O$
RTI-4229-286
DA 20.7 ± 0.57
5-HT 5062 ± 485
$NE_N$ 1231 ± 91
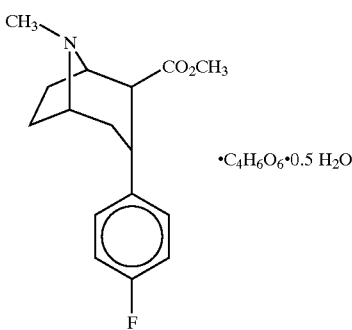
•$C_4H_6O_6$•0.5 $H_2O$
RTI-4229-287
DA 325 ± 20
5-HT 1686 ± 140
$NE_N$ 17.819 ± 440
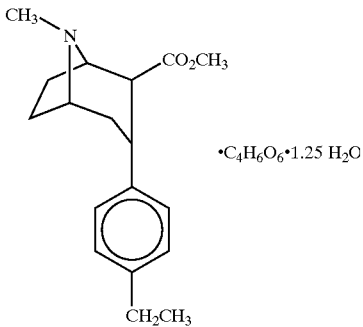
•$C_4H_6O_6$•1.25 $H_2O$
RTI-4229-296
BIH-141-1
DA 5.29 ± 0.53
5-HT 11.39 ± 0.28
$NE_N$ 1592.23 ± 93.4
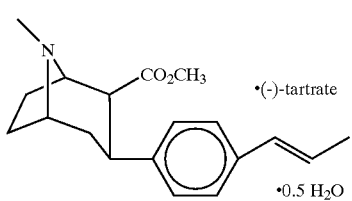
•(-)-tartrate
•0.5 $H_2O$
RTI-4229-304
BIH-141-11
DA 15.04 ± 1.2
5-HT 7.09 ± 0.71
$NE_N$ 2799 ± 300
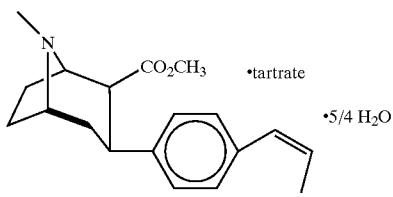
•tartrate
•5/4 $H_2O$ -continued
RTI-4229-305
BIH-141-18
DA  1.24 ± 0.11
5-HT 1.59 ± 0.2
$NE_N$ 21.8 ± 1.0
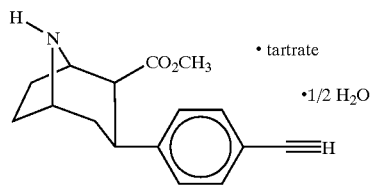
• tartrate
•1/2 $H_2O$
RTI-4229-307
BIH-141-15
DA  6.11 ± 0.67
5-HT 3.16 ± 0.33
$NE_N$ 115.8 ± 5.1
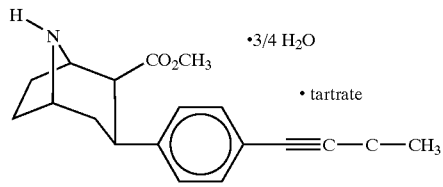
•3/4 $H_2O$
• tartrate
RTI-4229-309
BIH-141-17
DA  1.73 ± 0.05
5-HT 2.25 ± 0.17
$NE_N$ 14.9 ± 1.18
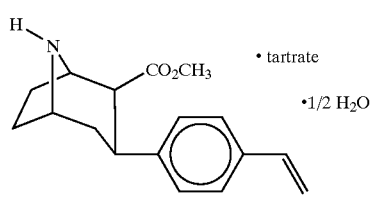
• tartrate
•1/2 $H_2O$
RTI-4229-318
DA  0.51 ± 0.03
5-HT 0.80 ± 0.06
$NE_N$ 21.1 ± 1.0
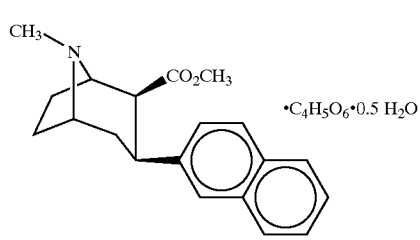
•$C_4H_5O_6$•0.5 $H_2O$
RTI-4229-330
DA  310.2 ± 21
5-HT 15.1 ± 0.97
$NE_N$  ±
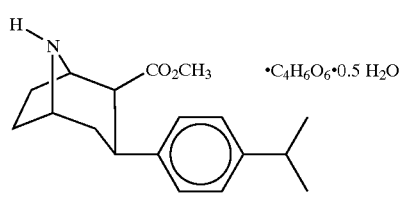
•$C_4H_6O_6$•0.5 $H_2O$
RTI-4229-422
DA  1.96
5-HT 1,100
$NE_N$ 6090
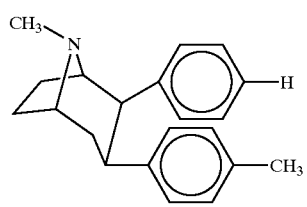

Particularly preferred compounds include RTI-4229-77, 87, 113, 114, 117, 119, 120, 124, 125, 126, 130, 141, 143, 144, 151, 152, 154, 165, 171, 176, 177, 180, 181, 194, 202, 252, 295, 298, 319, 334, 335, 336, 337, 338, 345, 346, 347, 348, 352 and 353. The chemical structures of these compounds are given below:
RTI-4229-77
DA 2.51 ± 0.25
5-HT ±
$NE_N$ 2,246.86 ± 238.99
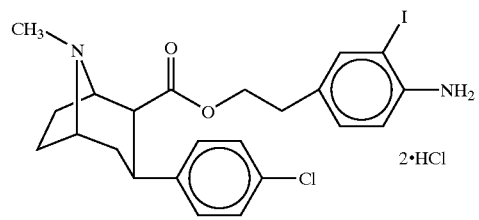
RTI-4229-87
DA 204 ± 29
5-HT 28,391 ± 2.324
$NE_N$ 35,782 ± 6.245
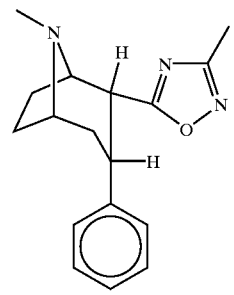
RTI-4229-113
DA 1.98 ± 0.05
5-HT 2,333.6 ± 176
$NE_N$ 2,955 ± 223
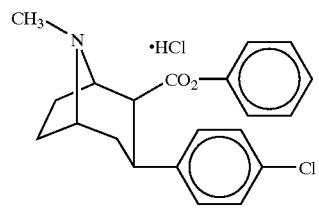
RTI-4229-114
DA 1.40 ± 0.13
5-HT 1,404 ± 7.1
$NE_N$ 778 ± 21
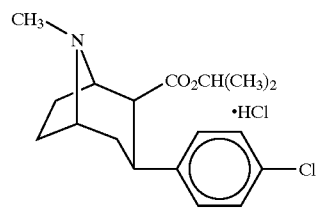
RTI-4229-117
DA 6.45 ± 0.85
5-HT 6,090 ± 488
$NE_N$ 1,926 ± 38
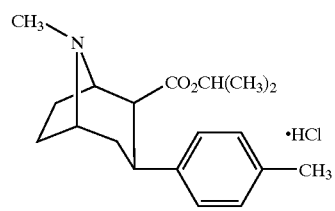
RTI-4229-119
DA 167 ± 13
5-HT 40,615 ± 9.416
$NE_N$ 6,985 ± 635
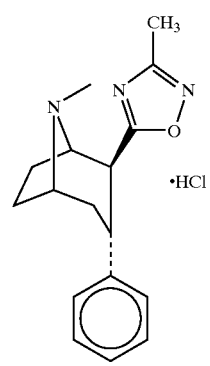

-continued
RTI-4229-120
DA 3.26 ± 0.06
5-HT 24,471 ± 1.515
NE$_N$ 5,833 ± 373
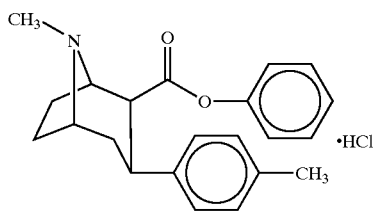
RTI-4229-124
DA 1,028 ± 65
5-HT 33,085 ± 5.434
NE$_N$ 70,993 ± 3.563
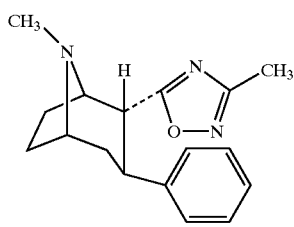
RTI-4229-125
DA 4.05 ± 0.57
5-HT 2,584 ± 799
NE$_N$ 363 ± 36
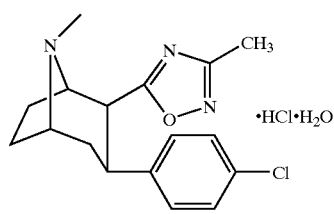
RTI-4229-126
DA 100 ± 6.3
5-HT 3,824 ± 418
NE$_N$ 7,876 ± 551
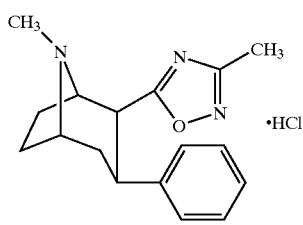
RTI-4229-130
DA 1.62 ± 0.02
5-HT 195 ± 4.8
NE$_N$ 245 ± 13
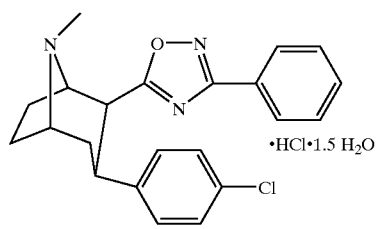
RTI-4229-141
DA 1.81 ± 0.19
5-HT 337 ± 43
NE$_N$ 835 ± 7.5
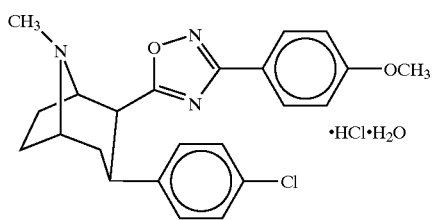
RTI-4229-143
DA 4.1 ± 0.22
5-HT 404 ± 58
NE$_N$ 4,069 ± 177
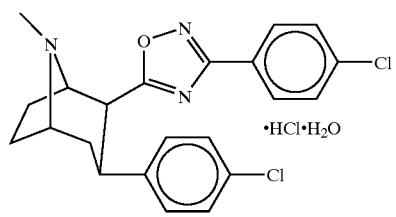

-continued
RTI-4229-144
DA 3.44 ± 0.36
5-HT 106 ± 10
NE$_N$ 1,825 ± 166
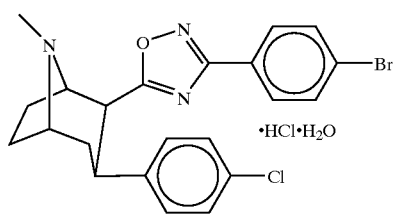
·HCl·H$_2$O
RTI-4229-151
DA 2.33 ± 0.26
5-HT 1,074 ± 125
NE$_N$ 60 ± 2
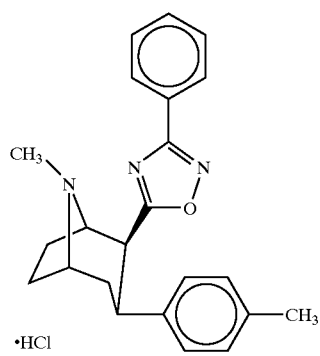
·HCl
RTI-4229-152
DA 494 ± 37
5-HT 1[.],995 ± 109
NE$_N$ 22,689 ± 1.957
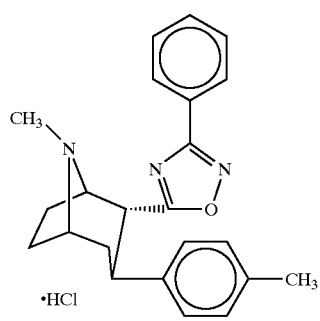
·HCl
RTI-4229-154
DA 6.0 ± 0.55
5-HT 3,460 ± 245
NE$_N$ 135 ± 13
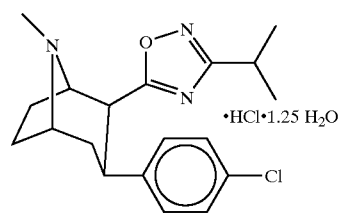
·HCl·1.25 H$_2$O
RTI-4229-171
DA 0.93 ± 0.09
5-HT 3,818.25 ± 346.14
NE$_N$ 254 ± 31
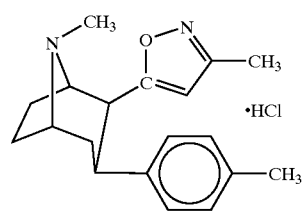
·HCl
RTI-4229-176
DA 1.58 ± 0.02
5-HT 5,109.72 ± 187.101
NE$_N$ 398 ± 17.6
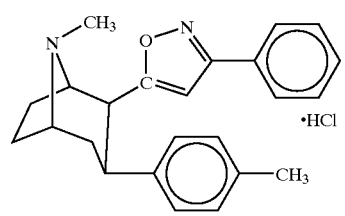
·HCl -continued
RTI-4229-177
DA 1.28 ± 0.18
5-HT 2,418.21 ± 135.68
NE$_N$ 504 ± 29
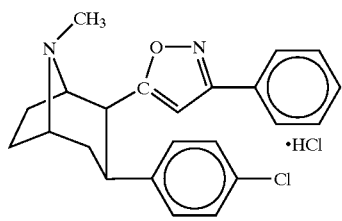
RTI-4229-180
DA 0.73 ± 0.04
5-HT 36.35 ± 4.99
NE$_N$ 67.9 ± 5.25
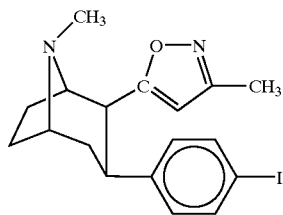
RTI-4229-181
DA 2.57 ± 0.14
5-HT 100 ± 9.0
NE$_N$ 868 ± 95
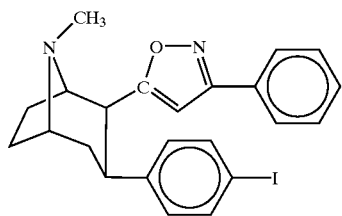
RTI-4229-194
DA 4.45 ± 0.12
5-HT 4,884.47 ± 155.42
NE$_N$ 253 ± 18.9
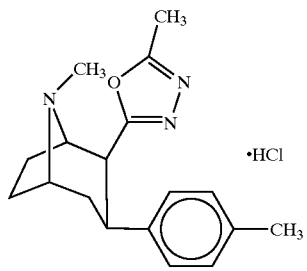
RTI-4229-202
DA 1.37 ± 0.14
5-HT 1,118.85 ± 120.00
NE$_N$ 402.8 ± 29.5
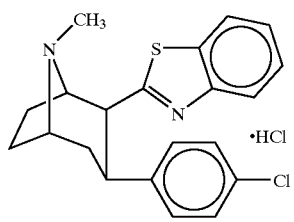
RTI-4229-295
BIH 141-4
DA 21.31 ± 0.87
5-HT 2.96 ± 0.04
NE$_N$ 1349 ± 105
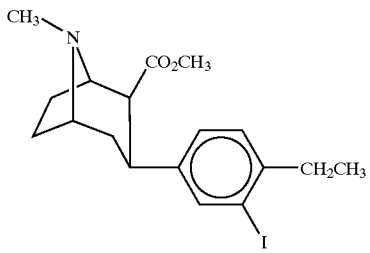

-continued
RTI-4229-298
BIH-141-4
DA 3.7 ± 0.16
5-HT 46.8 ± 5.8
$NE_N$ 346.6 ± 25
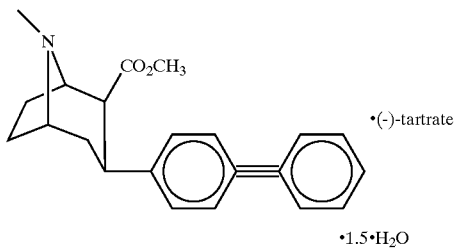
•(−)-tartrate
•1.5•$H_2O$
RTI-4229-319
DA 1.1 ± 0.09
5-HT 11.4 ± 1.3
$NE_N$ 70.2 ± 6.28
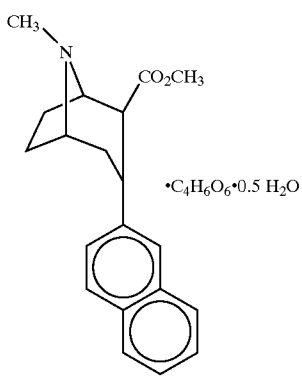
•$C_4H_6O_6$•0.5 $H_2O$
RTI-4229-334
DA 0.50 ± 0.03
5-HT 3086 ± 153
$NE_N$ 120 ± 10.4
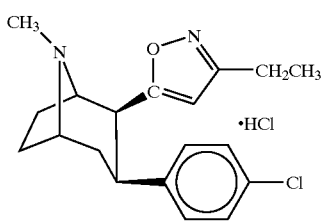
•HCl
RTI-4229-335
DA 1.19 ± 0.12
5-HT 2318 ± 153
$NE_N$ 954 ± 97.3
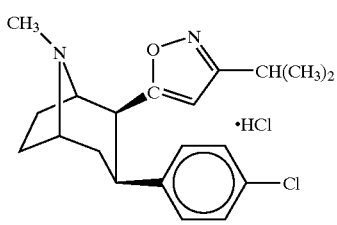
•HCl
RTI-4229-336
DA 4.09 ± 0.44
5-HT 5741 ± 421
$NE_N$ 1714 ± 38.5
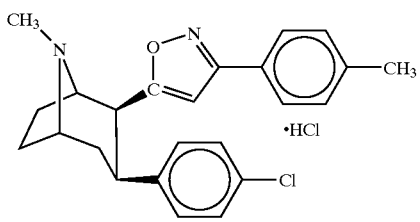
•HCl
RTI-4229-337
DA 7.31 ± 0.61
5-HT 36,842 ± 3616
$NE_N$ 6321 ± 703
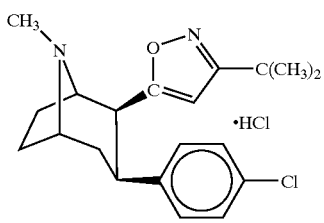
•HCl -continued
RTI-4229-338
DA 1104.2 ± 54.6
5-HT 7.41 ± 0.55
NE$_N$ 3366 ± 584
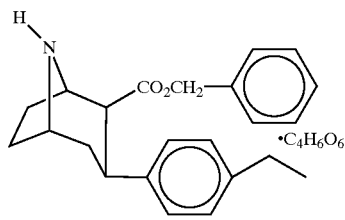
RTI-4229-345
DA 6.42 ± 0.46
5-HT > 76,000 ±
NE$_N$ 5290.4 ± 448.99
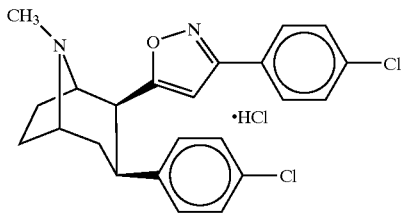
RTI-4229-346
DA 1.57 ± 0.10
5-HT 5880 ± 179
NE$_N$ 762.01 ± 37.8
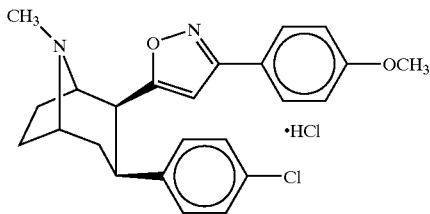
RTI-4229-347
DA 1.86 ± 0.09
5-HT 7256.95 ± 210
NE$_N$ 918.4 ± 108.34
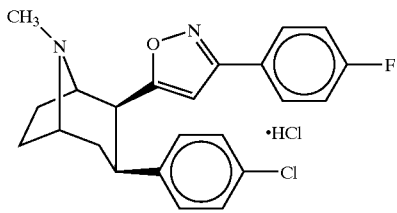
RTI-4229-348
DA 28.2 ± 1.9
5-HT 34,674 ± 3954
NE$_N$ 2667.2 ± 6267.3
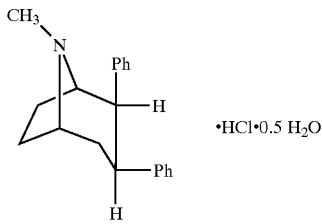
RTI-4229-352
DA 2.86 ± 0.21
5-HT 64.9 ± 1.97
NE$_N$ 52.4 ± 4.9
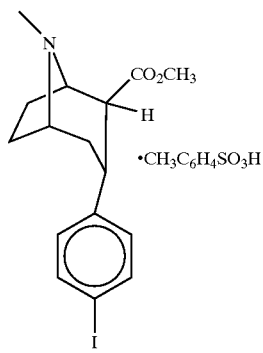

RTI-4229-353
DA 330.54 ± 17.12
5-HT 0.69 ± 0.07
NE$_N$ 148.4 ± 9.15

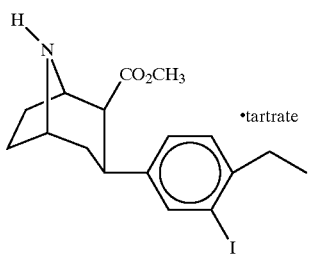

It should be noted that compound RTI-353 is a highly potent compound at the serotonin site, and is selective relative to the dopamine and norepinephrine sites. This compound is particularly useful as an antidepressant, and as an imaging agent for serotonin transporters.

Having generally described this invention, a further understanding can be obtained by reference to certain specific examples which are provided herein for purposes of illustration only and are not intended to be limiting unless otherwise specified.

EXAMPLES

All certified grade reagents or solvents were purchased from Aldrich Chemical Co. or Fluka Chemical Co. All reagents were normally used without further purification. When anhydrous conditions were required, solvents were distilled and dried by standard techniques immediately prior to use.

All air and moisture sensitive reactions were conducted under a prepurified nitrogen atmosphere in flame-dried glassware, previously dried at 150° C. Anhydrous solvents were transferred using conventional syringe or steel canula techniques under an inert atmosphere. Removal of solvents in vacuo was done on a Buchi rotavapor rotary evaporator operated at water aspirator pressure.

$^1$H NMR and 13C NMR spectra were recorded at 250 Mhz on a Bruker AM250 spectrometer. Optical rotations were recorded on at the Sodium D line on a Rudolph Research Autopol III polarimeter (1 dm cell). Melting point was recorded on a Uni-melt Thomas Hoover capillary melting point apparatus in open capillary tubes and were uncorrected. Elemental analysis were performed by Atlantic Microlab, Inc., Norcross, Ga.

Reaction products were purified by flash column chromatography using silica gel (mesh size 230–400) purchased from VWR Scientific. Thin layer chromatography (TLC) was performed on Whatman 254 nm fluorescent silica gel 60A (1×3 inches, 250 [μm thickness]) precoated TLC plates using the solvent systems indicated. Developed chromatograms were evaluated under 254 nm UV light or with iodine.

Example 1
General Procedure for the Preparation of Amides

To a solution of 1 mmol of 3β-(4-Chlorophenyl)-tropane-2β-carboxylic acid or 3β-(4-Methylphenyl)-tropane-2β-carboxylic acid in 5 ml of methylene chloride was added dropwise with stirring under nitrogen 2.0 eq oxalyl chloride (2 M solution in methylene chloride). The resulting solution was stirred at room temperature for an hour after evolution of gas has ceased. The solvent was removed in vacuo at room temperature and then at high vacuum to remove residual traces of oxalyl chloride. The resulting residue of acid chloride was suspended in 5 ml methylene chloride under nitrogen at 0° C., and 2.0 eq of the amine hydrochloride containing 4.0 eq of triethylamine, or 2.5 eq of the amine free base was added. The mixture was stirred at room temperature overnight. Aqueous 3N NaOH (5 ml) was added to basify the reaction mixture, the organic layer was separated and the aqueous layer extracted with 3×10 ml chloroform. The combined organic layers were dried (Na$_2$SO$_4$), filtered and the solvent removed in vacuo to give crude product. The crude was purified by flash column chromatography or crystallization.

Example 2
3β-(4-Chlorophenyl)-2β-(5-phenyl-1,3,4-oxadiazol-2-yl)-tropane Hydrochloride (RTI-188)

To a solution of 0.59 g (2 mmol) of 3β-(4-Chlorophenyl)-tropane-2β-carboxylic acid (chloro acid) in 2 ml of POCl$_3$ was added 0.31 g (2.2 mmol) of N-benzoic hydrazide and refluxed under nitrogen for 2 hours. The reaction mixture was cooled, poured into ice and rendered basic to pH 7–8 using concentrated NH$_4$OH. To the ice cold aqueous layer was added 10 ml brine and extracted thrice with 10 ml methylene chloride. The organic layers were combined dried (NaSO$_4$), filtered, and the solvent removed in vacuo to give 0.9 g of crude residue. Purification of the residue by flash column chromatography [50% (ether/triethylamine 9:1) in hexane] gave 0.33 g (42%) of pure oxadiazole (RTI-188) which was recrystallized from ether/petroleum ether: $^1$H NMR (CDCl$_3$) 1.81 (m, 3H), 2.18 (s, 3 H), 2.26 (m, 2H), 2.66 (m, 1H), 3.33 (m, 2H), 3.51 (m, 2 H), 7.16 (m, 4H) 7.45 (m, 3H), 7.86 (m, 2H); IR (CHCl$_3$) 2950, 1550, 1490, 1450, 1340, 1090 cm$^{-1}$; [β]$_D$–106.250 (c=0.08, CHCl$_3$)

The oxadiazole was converted into hydrochloride salt: $^1$H NMR (MeOD) 2.08 (m, 1H), 2.57 (m, 5H), 3.0 (s, 3H), 4.01 (m, 2H), 4.15 (m, 1H), 4.39 (m, 1H), 7.24 (m, 4H), 7.52 (m, 5H): mp 160–162° C.; Anal calcd for C$_{22}$H$_{23}$Cl$_2$N$_3$O.0.75H$_2$O; C=61.47; H=5.74, N=9.78; Cl=16.50; found C=61.47, H=5.73, N=9.76; Cl=16.56; [α]$_D$+84.59° (c=0.36, CH$_3$OH).

Further elution gave as a second fraction 0.1 g (13%) of white solid which was characterized to be 3X-(4-Chlorophenyl)-2β-(5-phenyl-1,3,4-oxadiazol-2-yl)-tropane: $^1$H NMR (CDCl$_3$) 1.76 (m, 3H), 2.06 (s, 3H), 2.45 (s, 3H), 3.36 (m, 2H), 3.51 (m, 1H), 3.65 (m, 1H), 7.21 (m, 4H), 7.47 (m, 3H) 7.91 (m, 2H); mp 170–171° C.; Anal calcd for C$_{22}$H$_{22}$ClN$_3$O; C=69.55; H=5.84, N=11.06; Cl=9.33; found C=69.49, H=5.85, N=11.01; Cl=9.41; [α]$_D$+33.06° (c=0.18, CHCl$_3$)

Example 3
3β-(4-Methylphenyl)-2β-(5-phenyl-1,3,4-oxadiazol-2-yl)-tropane Hydrochloride (RTI-195)

Reaction of 0.65 g (2.5 mmol) of 3D-(4-Methylphenyl)-tropane-2β-carboxylic acid (Methyl acid) as described above for RTI-188 gave after work-up and purification by flash column chromatography [(50% (ether/triethylamine 9:1) in hexane] 0.36 g (40%) of pure oxadiazole (RTI-195) which was recrystallized from ether/petroleum ether: $^1$H NMR (CDCl$_3$) 1.83 (m, 3H), 2.18 (s, 3H), 2.21 (s, 3H), 2.3 (m, 2H), 2.67 (m, 1H), 3.33 (m, 1H), 3.41 (m, 1H), 3.53 (m, 1H), 3.61 (m, 1 H) 7.0 (m, 2H).7.13 (m, 2H), 7.44 (m, 3H), 7.86 (m, 2H); IR (CHCL$_3$) 2990, 1545, 1505, 1440, 1350. cm$^{-1}$; $[\alpha]_D$–163.920 (c=0.2, CHCl$_3$)

The oxadiazole was converted into hydrochloride salt: H NMR (MeOD) 2.05 (m, 1H), 2.21 (s, 3H), 2.51 (m, 5H), 2.99 (s, 3H), 3.86 (m, 1H), 3.95 (m, 1H), 4.14 (m, 1H), 4.35 (m, 1H), 7.02 (m, 4H) 7.53 (m, 5H); mp 175–178° C.; Anal calcd for C$_{23}$H$_{26}$ClN$_3$O.0.75H$_2$O; C=67.47; H=6.77, N=10.26; Cl=8.66; found C=67.58, H=6.79, N=10.34; Cl=8.78; $[\alpha]_D$+97.220 (c=0.25, CH$_3$OH).

Further elution gave as a second fraction 0.18 g (20%) of solid which was characterized to be 3β-(4-Methylphenyl)-2β-(5-phenyl-1,3,4-oxadiazol-2-yl)-tropane which was recrystallized from ether/petroleum ether: $^1$H NMR (CDCl$_3$) 1.77 (m, 2H), 2.0 (m, 4H), 2.25 (s, 3H), 2.47 (s, 3H), 3.33 (m, 2H), 3.51 (m, 1H), 3.69 (d of d, J=2.6, 12 Hz, 1H), 6.91 (m, 2H) 7.03 (m, 2H).7.45 (m, 2H), 7.45 (m, 3H), 7.89 (m, 2H); IR (CHCL$_3$) 3020, 1540, 1510, 1415, 1250, 1215. cm; Anal calcd for C$_{23}$H$_{25}$N$_3$O; C=76.85; H=7.01, N=11.69; found C=76.60, H=7.12, N=11.55; $[\alpha]_D$+40.730 (C=0.28, CHCl$_3$)

Example 4
3β-(4-Methylphenyl)-2β-(5-methyl-1,3,4-oxadiazol-2-yl)-tropane Hydrochloride (RTI-194)

Reaction of 0.65 g (2.5 mmol) of methyl acid as described above for RTI-195 using 0.21 g (2.75 mmol) of N-acetic hydrazide gave after work-up and Purification by flash column chromatography [(75% (ether/triethylamine 9:1) in hexane] 0.29 g (39%) of pure oxadiazole (RTI-194) which was recrystallized from ether/petroleum ether: $^1$H NMR (CDCl$_3$) 1.75 (m, 3H), 2.18 (s, 3H), 2.22 (s, 3H), 2.25 (m, 2H), 2.35 (s, 3H), 2.56 (m, 1H), 3.24 (m, 1H), 3.4 (m, 2H), 3.47 (m, 1H) 7.0 (m, 4H); $^{13}$C NMR (CDCl$_3$) 11.06, 20.9, 25.08, 26.32, 34.11, 34.6, 41.83, 45.73, 61.97, 66.21, 127.11, 128.85, 135.85, 138.19, 162.5, 167.44; IR (CHCL$_3$) 2950, 1590, 1510, 1450, 1350, 1215 cm$^{-1}$; $[\alpha]_D$–108.470 (c=0.14, CHCl$_3$).

The oxadiazole was converted into hydrochloride salt: $^1$H NMR (MeOD) 1.99 (m, 1H), 2.23 (s, 3H), 2.27 (s, 3H), 2.47 (m, 5H), 2.94 (s, 3H), 3.72 (m, 1H), 3.79 (m, 1H), 4.10 (m, 1H), 4.23 (m, 1H), 7.05 (m, 4H); mp 146° C.(dec); Anal calcd for Cl$_8$H$_{24}$ClN$_3$O.0.5H$_2$O; C=63.06; H=7.35, N=12.26; Cl=10.34; found C=63.21, H=7.40, N=12.07; Cl=10.27; $[\alpha]_D$–43.05° (c=0.15, CH$_3$OH).

Example 5
3β-(4-Chlorophenyl)-2β-(S-phenyl-1,3,4-thiadiazol-2-yl)-tropane Hydrochloride (RTI-200).

Reaction of 0.59 g (2 mmol) of 3β-(4-Chlorophenyl) tropane-2β-carboxylic acid as described above for the preparation of amides gave after purification of the crude by crystallizing from ethyl acetate/ether 0.52 g (66%) of pure N-[3β-(4-Chlorophenyl)-tropane-2β-carboxylic]-N'-benzoylhydrazide: $^1$H NMR (CDCl$_3$) δ 1.76 (m, 3H), 2.24 (m, 2H), 2.41 (s, 3H) 2.51 (m, 1H), 2.68 (m, 1H), 3.18 (m, 1H), 3.44 (m, 2H), 7.22 (m, 4H), 7.46 (m, 3H), 7.78 (m, 2H), 9.02 (br s, 1H), 12.97 (br s, 1H); IR (CHCl$_3$) 3385, 3035, 3000, 1620, 1570, 1485, 1450, 1215 cm$^{-1}$.

A solution of 0.4 g (1 mmol) of N-[3D-(4-Chlorophenyl)-tropane-2β-carboxylic]-N'-benzoyl-hydrazide and 0.8 g (2 mmol) of Lawesson's reagent in 10 ml toluene was refluxed for 4 h under nitrogen. The reaction mixture was cooled and solvent removed in vacuo to give a yellow residue. To the residue was added 3 g of silica gel and 10 ml of methylene chloride, the resulting slurry was mixed properly and the solvent removed in vacuo. The crude compound impregnated on silica gel was loaded on a column and purified by flash column chromatography [50% ether/triethylamine (9:1) in hexane] to obtain 0.23 g (58%) of pure thiadiazole (RTI-200) which was further purified by recrystallizing from ether: $^1$H NMR (CDCl$_3$) δ 1.75 (m, 3H), 2.20 (m, 3H), 2.32 (s, 3H), 3.30 (m, 3H), 3.78 (m, 1H), 6.86 (m, 2H), 7.08 (m, 2H), 7.43 (m, 3H), 7.97 (m, 2H); NMR 25.55, 25.88, 34.60, 36.09, 41.55, 49.73, 61.48, 65.33, 127.59, 128.28, 128.78, 128.88, 130.37, 130.88, 132.19, 139.27, 168–29, 169.56; IR (CCl$_4$) 2940, 1490, 1460, 1340, 1245, 1100, 1010 cm$^1$ The thiadiazole was converted into hydrochloride salt: $^1$H NMR (MeOD) δ 2.06 (m, 1H), 2.53 (m, 5H), 2.97 (s, 3H), 3.92 (m, 1H), 4.17 (m, 2H), 4.39 (m, 1H), 7.11 (m, 2H), 7.26 (m, 2H), 7.51 (m, 3H), 7.79 (m, 2H); mp 165–170° C.; Anal calcd for C$_{22}$H$_{23}$Cl$_2$N$_3$S.0.75H$_2$O; C=59.26, H=5.54, N 9.42, Cl=15.90; S=7.19. found C=59.27, H=5.52, N=9.40, Cl=15.99; S 7.09; [°]$_D$–42.81° (c=0.16, MeOH).

Further elution gave 0.08 g (21%) as a second fraction which was characterized to be 3β-(4-chlorophenyl)-2β-(5-phenyl-1,3,4-oxadiazol-2-yl)-tropane.

Example 6
3β-(4-Methylphenyl)-2β-(5-phenyl-1,3,4-thiadiazol-2-yl)-tropane Hydrochloride (RTI-199)

Reaction of 0.65 g (2.5 mmol) of 3β-(4-Methylphenyl)-tropane-2β-carboxylic acid as described above for preparation of amides gave after work up and purification by flash column chromatography [(50% CMA-80 in methylene chloride)] 0.48 g (51%) pure N-[3β-(4-Methylphenyl) Tropane-2β-carboxylic]-N'-benzoyl-hydrazide which was further purified by recrystallizing from ether/pet ether: $^1$H NMR (CDCl$_3$) δ 1.75 (m, 3H), 2.20 (m, 2H), 2.27 (s, 3H), 2.42 (s, 3H), 2.51 (m, 1 H), 2.67 (m, 1H), 3.18 (m, 1H), 3.47 (m, 2H), 7.11 (m, 4 H), 7.48 (m, 3H), 7.81 (m, 2H), 9.06 (br s, 1H), 13.09 (br s, 1H); IR (CHCl$_3$) 3385, 3045, 1625, 1570, 1460, 1420, 1100 cm$^{-1}$;

Reaction of 0.29 g (0.75 mmol) of N-[3β-(4-Methylphenyl)-tropane-2β-carboxylic]-N'-benzoyl-hydrazide as described above for RTI-200 gave after work and purification by flash chromatography [40% ether/triethylamine (9:1) in hexane] 0.16 g (58%) of pure thiadiazole (RTI-199): $^1$H NMR (CDCl$_3$) δ 1.70 (m, 1H), 1.88 (m, 2H), 2.20 (s, 3H), 2.23 (m, 2H), 2.21 (s, 3H), 2.38 (m, 1H), 3.21 (m, 1H), 3.32 (m, 1H), 3.39 (m, 1H), 3.78 (m, 1H), 6.81 (m, 2H), 6.92 (m, 2H), 7.43 (m, 3H), 7.97 (m, 2H); $^{13}$C NMR 20.98, 25.65, 25.95, 34.79, 36.25, 41.65, 50.05, 61.68, 65.49, 127.32, 127.65, 128.89, 128.95, 130.29, 131.11, 135.94, 137.68, 168.83, 169.45; IR (CCl$_4$) 2935, 1510, 1450, 1250, 1120, 1100, 1060 cm$^{-1}$ The thiadiazole was converted into hydrochloride salt; $^1$H NMR (MeOD) δ 1.95 (m, 1H), 2.17 (s, 3H), 2.41 (m, 5H), 2.89 (s, 3H), 3.76 (m, 1H), 4.05 (m, 2H), 4.30 (m, 1H), 4.22 (m, 1H), 6.89 (m, 2H), 6.99 (m, 2H), 7.39 (m, 3H), 7.67 (m, 2H); mp 180–185° C.; Anal calcd for C$_{23}$H$_{26}$ClN$_3$S.H$_2$O; C=65.62, H=6.46, N=9.98, Cl=18.42; S=7.62. found C=65.57, H=6.63, N=9.91, Cl=18.24; S=7.55; $[\alpha]_D$–33.5° (c=0.2, MeOH)

Further elution gave 0.04 g (15%) of a second fraction which was characterized to be 3β-(4-Methylphenyl)-2β(5-phenyl-1,3,4-oxadiazol-2-yl)-tropane.

Example 7
3β-(4-Chlorophenyl)-2β-(5-phenyl-oxazol-2-yl)-tropane Tartrate RTI-189)

Reaction of 0.73 g (2.5 mmol) of 35-(4-Chlorophenyl)-tropane-2β carboxylic acid as described above for the preparation of amides gave after purification by flash column chromatography (15% CMA 80 in methylene chloride) 0.8 g (81%) of pure 3β-(4-Chlorophenyl)-tropane-2β-N-(phenyacyl)carboxamide: $^1$H NMR (CDCl$_3$) δ 1.71 (m, 3H), 2.19 (m, 2H), 2.39 (5, 3H), 2.46 (m, 1H), 2.58 (m, 1H), 3.13 (m, 1H), 3.43 (m, 2H), 4.74 (m, 2H), 7.13 (m, 4H), 7.49 (m, 2H), 7.59 (m, 1H), 7.96 (m, 2H), 10.57 (br s, 1H); IR (CHCl$_3$) 3135, 3010, 2930, 1695, 1650, 1590, 1530, 1485, 1450, 1355, 1220 cm$^1$.

A solution of 0.725 g (1.83 mmol) of 3β-(4-Chlorophenyl)-tropane-2β-N(phenyacyl)carboxamide in 6 ml POCl$_3$ was heated at 125° C. under nitrogen for 2 hours. The reaction mixture was cooled and poured into ice and rendered basic to pH 7–8 using concentrated NH$_4$OH. To the ice cold aqueous layer was added 10 ml brine and extracted thrice with 10 ml methylene chloride. The organic layers were combined dried (NaSO$_4$), filtered, and the solvent removed in vacuo to 0.63 g crude oxazole. Purification of the crude by flash column chromatography [(40% (ether/triethylamine 9:1) in hexane] gave 0.34 g (49%) of pure oxazole (RTI-189) which was further purified by recrystallizing from ether/petroleum ether: $^1$H NMR (CDCl$_3$) 1.79 (m, 3H), 2.22 (s, 3H), 2.27 (m, 2H), 2.66 (m, 1H), 3.27 (m, 1H), 3.40 (m, 2H), 3.53 (m, 1H), 7.11 (s, 1H), 7.16 (s, 4H) 7.31 (m, 5H); IR (CHCl$_3$) 2950, 1540, 1490, 1445, 1350, 1120, 1090 CM$^{-1}$; [α]$_D$−70.37° (c=0.19, CHCl$_3$)

The oxazole was converted into tartrate salt: $^1$H NMR (MeOD) 2.14 (m, 1H), 2.54 (m, 5H), 2.96 (s, 3H), 3.75 (m, 2 H), 4.12 (m, 1H), 4.25 (m, 1H), 4.41 (s, 2H), 7.05 (m, 2 H), 7.29 (m, 7H), 7.45 (s, 1H), 7.43 (s, 1H); mp 126° C. (dec); Anal calcd for C$_{27}$H$_{29}$ClN$_2$O$_7$.0.75H$_2$O; C=59.78; H=5.67, N=5.16; Cl=6.54; found C=59.78, H=5.58, N=4.93; Cl=6.31; [α]$_D$+101.43° (c=0.21, CH$_3$OH)

Example 8
3β-(4-Methylphenyl)-2β-(5-phenyl-oxazol-2-yl)-tropane Tartrate (RTI-178)

Reaction of 0.52 g (2 mmol) of 3β-(4-Methylphenyl)-tropane-2β-carboxylic acid as described above for preparation of amides gave after work up and purification by flash column chromatography (15% CMA in methylene chloride) 0.54 g (72%) of pure 3β-(4-Methylphenyl)-tropane-2β-N-(phenyacyl)carboxamide: $^1$H NMR (CDCl$_3$) δ 1.73 (m, 3H), 2.14 (m, 2H), 2.26 (s, 3H), 2.40 (s, 3H), 2.47 (m, 1H), 2.59 (m, 1H), 3.14 (m, 1H), 3.42 (m, 2H), 4.74 (m, 2H), 7.05 (m, 4H), 7.48 (m, 2H), 7.59 (m, 2H), 7.97 (m, 2H), 10.62 (br s, 1H); IR (CHCl$_3$) 3155, 3005, 2930, 1690, 1650, 1520, 1450, 1355, 1215 cm$^{-1}$ Reaction of 0.5 g (1.33 mmol) of 3D-(4-Methylphenyl)-tropane-2β-N-(phenyacyl)carboxamide as described above for RTI-189 gave after workup and purification by flash column chromatography [(40% (ether/triethylamine 9:1) in hexane] 0.1 g (31%) RTI-158 as a first fraction. Further elution gave 0.19 g (42%) of pure oxazole RTI-178: $^1$H NMR (CDCl$_3$) 1.8 (m, 3 H), 2.18 (m, 2H), 2.21 (s, 3H), 2.22 (s, 3H), 2.67 (m, 1 H), 3.28 (m, 1H), 3.42 (m, 2H), 3.53 (m, 1H), 6.98 (m, 2 H), 7.11 (m, 3H), 7.30 (m, 5H).

The oxazole was crystallized as the tartrate salt: $^1$H NMR (MeOD) 1.99 (m, 1H), 2.19 (s, 3H), 2.54 (m, 5H), 2.95 (s, 3 H), 3.74 (m, 2H), 4.13 (m, 1H), 4.26 (m, 1H), 4.4 (s, 2H), 6.91 (m, 2H), 7.0 (m, 2H), 7.25 (m, 2H), 7.33 (m, 3H), 7.43 (s, 1H); mp 175–181 C; Anal calcd for C$_{28}$H$_{32}$N$_2$O$_7$.1H$_2$O; C=63.87; H=6.51, N=5.32; found C=64.21, H=6.40, N=5.19; [α]$_D$−104.04° (c=0.6, CH$_3$OH)

Example 9
3β-(4-Chlorophenyl)-2β-(5-phenylthiazol-2-yl)-tropane Hydrochloride (RTI-219)

To a solution of 0.74 g (1.86 mmol) of 3β-(4-Chlorophenyl)-tropane-2β-N-(phenyacyl)carboxamide and 1.51 g (7.45 mmol) of Lawesson's reagent in 18 ml of toluene was refluxed under N$_2$ for 5 hours. The reaction mixture was cooled and solvent removed in vacuo to give crude residue. To the residue was added 3 g of silica gel and 10 ml of methylene chloride, the resulting slurry was mixed properly and the solvent removed in vacuo. The crude compound impregnated on silica gel was loaded on a column and purified by flash column chromatography [(40% (ether/triethylamine 9:1) in hexane] to give 0.21 g (30%) of pure thiazole RTI-219: $^1$H NMR (CDCl) 1.61 (m, 1H), 1.82 (m, 2H), 2.22 (m, 2H), 2.34 (s, 3H) 2.39 (m, 1H), 3.28 (m, 2H), 3.39 (m, 1H), 3.49 (m, 1H), 6.8 (m, 2H) 7.07 (m, 2H), 7.32 (m, 3H), 7.57 (m, 2H), 7.60 (s, 1H); $^{13}$C NMR (MeOD) 25.51, 25.99, 35.01, 36.92, 41.72, 52.97, 61.58, 65.70, 126.45, 127.60, 128.13, 128.89, 129.05, 131.91, 132.43, 136.11, 139.91, 140.27, 168.97; IR (CHCl$_3$) 2945, 1590, 1485, 1445, 1350, 1125, 1090. cm$^{-1}$.

The thiazole was converted into hydrochloride salt: $^1$H NMR (MeOD) 1.99 (m, 1H), 2.51 (m, 5H), 2.93 (s, 3H), 3.79 (m, 2 H), 4.15 (m, 1H), 4.28 (m, 1H), 7.02 (d, J=8.5 Hz, 2H) 7.21 (d, J=8.5 Hz, 2H), 7.39 (m, 5H), 8.06 (s, 1H); mp 228–230° C.; Anal calcd for C$_{23}$H$_{24}$ClN$_2$S.H$_2$O; C=61.47, H=5.83, N=6.23, S=7.13, Cl=15.78; found C=61.61, H=5.76, N=6.20, S=7.51, Cl=15.84; [α]$_D$+27.43° (c=0.11, CH$_3$OH)

Example 10
3β-(4-Chlorophenyl)-2β-(benzothiazol-2-yl)-tropane Hydrochloride (RTI-202)

Reaction of 0.59 g (2 mmol) of 3β-(4-Chlorophenyl)-tropane-2β-carboxylic acid as described above for preparation of amides gave after purification of the crude by flash column chromatography (50% CMA-80 in methylene chloride) 0.3 g (41%) of pure RTI-202 which was further purified by recrystallizing from ether/hexane: $^1$H NMR (CDCl$_3$) δ 1.65 (m, 1H), 1.87 (m, 2 H), 2.24 (m, 2H), 2.34 (s, 3H), 2.41 (m, 1H), 3.28 (m, 2 H), 3.40 (m, 1H), 3.62 (m, 1H), 6.8 (m, 2H), 6.81 (m, 2H), 7.29 (m, 2H), 7.70 (m, 1H), 7.84 (m, 1H); $^{13}$C NMR (CDCl$_3$) δ 25.58, 26.07, 35.40, 36.95, 41.56, 53.09, 61.57, 65.47, 120.95, 122.42, 124.11, 125.20, 128.05, 129.03, 131.87, 136.72, 139.91, 151.33, 171.11; IR (CHCl$_3$) 2940, 2795, 1495, 1445, 1305, 1130, 1105, 1015, 907 CM$^{-1}$; [α]$_D$−233.89° (c=0.09, CHCl$_3$).

The benzothiazole was converted into hydrochloride salt: $^1$H NMR (MeOD) δ 2.02 (m, 1H), 2.43 (m, 4H), 2.89 (m, 1H), 2.98 (s, 3H), 3.90 (m, 2H), 4.23 (m, 1H), 4.34 (m, 1H), 7.02 (m, 2H), 7.13 (m, 2H), 7.45 (m, 2H), 7.81 (m, 1H), 8.16 (m, 1H); mp 140–150° C. (dec); Anal calcd for C$_{21}$H$_{22}$Cl$_2$N$_2$S.0.75H$_2$O C=60.21, H=5.65, N=6.69, Cl=16.93; S=7.65: found C=60.14, H=5.74, N=6.60, Cl=16.89; S=7.71; [α]$_D$−1 72.49° (c 0.28, MeOH).

Example 11
3β-(4-Chlorophenyl)-tropane-2β-nitrile (RTI-161)

To a solution of 0.95 g (3.5 mmol) of 3D-(4-Chlorophenyl)-tropane-2β-carboxamide in 20 ml dry THF was added 0.56 ml (7 mmol) pyridine. To the resulting solution at room temperature was added dropwise with stirring under nitrogen 0.35 ml (4.2 mmol) of trifluoroacetic anhydride. The reaction was stirred at room temperature for 30 minutes, and quenched with 10 ml water. The solvent was removed under vacuo and the residue was taken in 10 ml saturated aqueous K$_2$CO$_3$ and extracted thrice with 10 ml CHCl₃. The organic layers were combined and washed with 20 ml brine dried (NaSO₄), filtered, and the solvent removed in vacuo to give 0.26 g crude product. Purification of the crude by flash column chromatography (10% CMA in methylene chloride) gave 0.68 g (77%) of pure nitrile RTI-161 which was recrystallized from methylene chloride and hexane: $^1$H is NMR (CDCl₃) δ 1.70 (m, 3H), 2.22 (m, 3H), 2.35 (s, 3H), 2.80 (m, 1H), 3.04 (m, 1H), 3.34 (m, 1H), 3.43 (m, 1H), 7.26 (m, 4H); IR (CHCl₃) 3700, 2950, 2225, 1490, 1470, 1090, 900 cm¹; mp 167–173° C.; Anal calcd for $C_{15}H_{18}Cl_2N_2.0.75H_2O$; C=57.98, H=6.32 N=9.02, Cl=22.82; found C=58.22, H=6.12, N=8.48, Cl=22.89; $[\alpha]_D$–73.33° (c=0.48, MeOH)

Example 12

3β-(4-Methylphenyl)-tropane-2β-nitrile Hydrochloride (RTI-158)

Reaction of 0.26 g (1 mmol) of 3β-(4-Methylphenyl)-tropane-2β-carboxamide as described above for RTI-161 gave after work up and purification 0.16 g (67%) of pure nitrile (RTI-158): $^1$H NMR (CDCl₃) δ 1.68 (m, 3H), 2.18 (m, 3H), 2.32 (s, 3H), 2.35 (s, 1H), 2.82 (m, 1H), 3.02 (m, 1H), 3.36 (m, 1H), 3.43 (m, 1H), 7.18 (m, 4H); IR (CHCl₃) 3675, 3000, 2950, 2200, 1600, 1510, 1450, 1350, 1220, 1100 cm⁻¹.

The crude product was crystallized as the HCl salt: $^1$H NMR (MeOH) δ 2.08–2.58 (m, 9H), 2.92 (s, 3H), 3.54 (m, 1H), 3.69 (br s, 1H), 4.12 (br s, 1H), 4.29 (m, 1H), 7.21 (m, 4 H); mp 270° C. (dec.); Anal calcd for $C_{16}H_2$, $CIN_2$; C 69.42, H=7.65 N=10.12, Cl=12.81; found C=69.31, H=7.70, N=10.12, Cl=12.81; $[\alpha]_D$–76.4° (c=0.5, MeOH).

Example 13

3β-(4-Chlorophenyl)-tropane-2β-tetrazole (RTI-163)

To a solution of 0.13 g 0.5 mmol) of RTI-161 in 5 ml dry THF was added 0.28 ml (5 mmol) azidotrimethylsilane and the mixture was placed in a PTFE-lined autoclave. The solution was heated to 150° C. for 24 hours in an oil bath. The reaction mixture was cooled and transferred using MeOH. The solvent was removed in vacuo to give a brownish residue. Purification of the crude by flash column chromatography (20%–50% CMA in methylene chloride) gave 0.05 g (33.) of pure tetrazole (RTI-163): $^1$H NMR (CDCl₃+1 drop MeOD) δ 1.73 (m, 1 H), 2.44–2.02 (m, 4H), 2.6 (m, 1H), 2.68 (s, 3H), 3.33 (m, 1H), 3.65 (m, 1H), 3.73 (m, 1H), 3.97 (m, 1H), 6.68 (d, J=8 Hz, 2H), 7.07 (d, J=8 Hz, 2H); mp 296–300° C.; Anal calcd for $C_{15}H_{18}CIN_5.0.75H_2O$; C=56.78, H=6.19 N=22.07, Cl=11.17; found C=56.69, H=6.22, N=22.09, Cl=11.15; $[\alpha]_D$–124.94° (c=0.39, MeOH).

Example 14

3β-(4-Methylphenyl)-tropane-2β-tetrazole Hydrochloride (RTI-157)

Reaction of 0.12 g (0.5 mmol) of RTI-158 as described above for RTI-163 gave after workup and purification of the crude by flash column chromatography (100% CMA) 0.14 g (88%) of pure tetrazole (RTI-157): $^1$H NMR (CDCl₃+1 drop MeOD) δ 1.8 (m, 1H), 2.14 (s, 3H), 2.35 (m, 5H), 2.71 (s, 3H), 3.36 (m, 1H), 3.75 (m, 2H), 4.02 (m, 1H), 6.48 (d, J=8 Hz, 2 H), 6.82 (d, J=8 Hz, 2H).

The purified product was converted into HCl salt: $^1$H NMR (MeOD) δ 2.01 (m, 1H), 2.27 (s, 3H), 2.69 (m, 5H), 2.97 (s, 3H), 3.81 (m, 2H), 4.18 (m, 2H), 5.5 (s, 1H), 6.76 (d, J=8 Hz, 2H), 7.02 (d, J=8 Hz, 2H); mp 212**C (dec); Anal calcd for $C_{16}H_{23}Cl_2N_5.0.25H_2O$; C=53.26, H=6.56 N=19.41; found C=53.41, H=6.50, N=19.02; $[\alpha]_D$–110.97° (c=0.16, MeOH).

Example 15

3β-(4-Chlorophenyl)-2β-(3-methylisoxazol-5-yl)tropane Hydrochloride (RTI-165)

A solution of n-butyl lithium in hexane 5.9 ml (2.5 M. 14.6 mmol) was added to a stirred solution of acetone oxime 0.55 g (7.3 mmol) in dry THF (15 ml) at 0° C. under nitrogen. After 1 hour, a solution of 1.65 g (5.62 mmol) 3β-(4-Chlorophenyl)-2β-(carbomethoxy)tropane in 10 ml dry was added dropwise with stirring at 0° C. The solution was allowed to warm to room temperature over 18 hours. The mixture was poured into a stirred solution of concentrated sulfuric acid (3.2 g) in THF (15 ml) and water (4 ml) and was heated under reflux for 1 hour. The cooled solution was made basic using saturated aqueous $K_2CO_3$ (10 ml) and extracted thrice with 10 ml methylene chloride. The combined organic layers were dried at $(Na_2SO_4)$, filtered and solvent removed in vacuo to give 1.8 g of crude isoxazole. Purification of the crude residue by flash column chromatography (10° CMA in methylene chloride) gave 0.74 g (46%) of pure isoxazole RTI-165 which was further purified by crystallization from methylene chloride/hexane: !H NMR (CDCl₃) δ 1.71 (m, 3H), 2.10 (m, 3H), 2.18 (s, 3H), 2.24 (s, 3H), 3.20 (m, 2H), 3.32 (m, 2H), 6.18 (s, 1H), 6.9 (d, J=8 Hz, 2H),7.14 (d, J=8, Hz, 2H); IR (CCl₄) 2950, 1590, 1490, 1420, 1350, 1020, 910 cm⁻¹; mp 154–156° C.; Anal calcd for $C_{18}H_{21}N_2OCl$; C=68.28, H=6.68, N=8.84, Cl=11.19; found C=68.22, H=6.69, N=8.87, Cl=11.19; $[\alpha]_D$–125.58° (c=0.43, MeOH).

The isoxazole was crystallized as the hydrochloride salt: $^1$H NMR (MeOD) δ 2.04 (s, 3H), 2.19 (m, 1H), 2.30 (m, 1H), 2.48 (m, 2H), 2.60 (m, 1H), 2.70 (m, 1H), 2.90 (s, 3H), 3.68 (m, 1H), 3.81 (m, 1H), 4.04 (m, 1H), 4.15 (m, 1H), 5.55 (s, 1H), 7.04 (d, J=8 Hz, 2H), 7.14 (d, J=8 Hz, 2 H); mp>235° C. (dec); Anal calcd for $C_{18}H_{22}Cl_2N_2O$; C=61.19, H=6.28, N=7.93, Cl=20.07; found c=60.98, H=6.38, N=15 7.91, Cl=19.96; $[\alpha]_D$–102.89° (c=0.46, MeOH)

Example 16

3β-(4-Methylphenyl)-2P-(3-methylisoxazol-5-yl)tropane Hydrochloride (RTI-171)

Reaction of 1.09 g (4 mmol) of 3β-(4-Methylphenyl)-2β-(carbomethoxy)tropane as described above for RTI-165 gave after workup 1.21 g crude isoxazole. Purification of the crude by flash column chromatography (15% CMA in methylene chloride) gave 0.73 g (62%) pure isoxazole (RTI-171): $^1$H NMR (CDCl₃) δ 1.73 (m, 3H), 2.11 (m, 3H), 2.17 (s, 3H), 2.23 (s, 3H), 2.25 (s, 3H), 3.20 (m, 2H), 3.32 (m, 2H), 6.13 (s, 1 H), 6.97 (m, 4H); IR (CCl₄) 2935, 2785, 1590, 1510, 1460, 1421, 1350, 1125, 1010, 910 cm⁻¹.

The isoxazole was crystallized as the hydrochloride salt: $^1$H NMR (MeOD) δ 2.01 (s, 3H), 2.24 (s, 3H), 2.32 (m, 2H), 2.42 (m, 4H), 2.81 (s, 3H), 3.61 (m, 1H), 3.78 (m, 1H), 4.03 (m, 1H), 4.15 (m, 1H), 5.45 (s, 1H), 6.96 (m, 4H); mp 277° C.; Anal calcd for $Cl_9H_{25}CIN_2O$; C=68.55, H=7.57, N 8.42, Cl=10.65; found C=68.65, H=7.62, N=8.42, Cl=10.56; $[\alpha]_D^{-107.28°}$ (c=0.71, MEOH)

Example 17

3β-(4-Iodophenyl)-2β-(3-methylisoxazol-5-yl)tropane Hydrochloride (RTI-180)

Reaction of 0.73 g (1.9 mmol) of 3β-(4-Iodophenyl)-2D-(carbomethoxy)tropane as described above for RTI-165 gave after workup 0.77 g of crude isoxazole. Purification of the crude by flash column chromatography (5% CMA80 in methylene chloride) gave 0.37 g (49%) of pure isoxazole RTI-180: $^1$H NMR (CDCl₃) δ 1.71 (m, 3H), 2.12 (m, 3H), 2.18 (s, 3H), 2.24 (s, 3H), 3.17 (m, 2H), 3.33 (m, 2H), 6.18 (s, 1H), 6.74 (m, 2 H), 7.49 (m, 2H); IR (CHCl₃) 2940, 1600, 1485, 1450, 1420, 1355 cm⁻¹.

The isoxazole was crystallized as the hydrochloride salt: $^1$H NMR (MeOD) δ 2.11 (s, 3H), 2.50 (m, 6H), 2.89 (s, 3H), 3.70 (m, 1H), 3.90 (m, 1H), 4.14 (m, 1H), 4.22 (m, 1H), 5.66 (s, 1H), 6.96 (m, 2H), 7.56 (m, 2H); mp >235° C. (dec); Anal calcd for $C_{18}H_{22}ClIN_2O\cdot0.25H_2O$ C=48.12, H 5.05, N=6.24, Cl=15.79; I=56.50; found C=47.84, H=5.05, N=6.19, Cl=15.77; I=56.46; [α]$_D$-94.57° (c=0.39, MeOH)

Example 18
3β-(4-Chlorophenyl)-2β-(3-phenylisoxazol-5-yl)tropane Hydrochloride (RTI-177)

Reaction of 1.18 g (4 mmol) of 3β-(4-Chlorophenyl)-2β-(carbomethoxy)tropane as described above for RTI-165 gave after work up 1.46 g of crude isoxazole. Purification of the crude by flash column chromatography [20% (ether/triethylamine 9:1) in hexane] gave 0.75 g (50%) of pure isoxazole RTI-177 which was further purified by crystallizing from ether/petroleum ether: $^1$H NMR (CDCl$_3$) δ 1.74 (m, 3H), 2.22 (m, 3H), 2.27 (s, 3H), 3.24 (m, 2H), 3.36 (m, 2H), 6.80 (s, 1 H), 6.94 (m, 2H), 7.12 (m, 2H), 7.40 (m, 3H), 7.76 (m, 2 H); IR (CHCl$_3$) 2940, 1600, 1590, 1490, 1450, 1405, 1350 cm$^{-1}$.

The isoxazole was crystallized as the hydrochloride salt: $^1$H NMR (MeOD) δ 2.35 (m, 6H), 2.84 (s, 3H), 3.73 (m, 1 H, 4.09 (m, 1H), 4.21 (m, 1H), 6.12 (s, 1H), 7.14 (m, 4H), 7.34 (m, 3H), 7.57 (m, 2H); mp 287° C.; Anal calcd for $C_{23}H_{24}Cl_2N_2O\cdot0.25H_2O$ C=65.79, H=5.88, N 6.67, Cl=16.89; found C=65.94, H=5.79, N=6.68, Cl=17.00; [α]$_D$-97.5° (c=0.28, MeOH).

Example 19
3β-(4-Methylphenyl)-2β-(3-phenylisoxazol-5-yl)tropane Hydrochloride (RTI-176)

Reaction of 1.09 g (4 mmol) of 3β-(4-Methylphenyl)-2β-(carbomethoxy)tropane as described above for RTI-165 gave after work up 1.56 g of crude isoxazole. Purification of the crude by flash column chromatography [25% (ether/triethylamine 9:1) in hexane] gave 1.1 g (77%) of pure isoxazole RTI-176 which was further purified by crystallizing from methylene chloride/hexane: $^1$H NMR (CDCl$_3$) δ 1.76 (m, 3H), 2.23 (m, 3H), 2.24 (s, 3H), 2.27 (s, 3H), 3.23 (m, 2H), 3.36 (m, 2H), 6.74 (s, 1H), 6.93 (m, 4H), 7.41 (m, 3H), 7.76 (m, 2H); IR (CCl$_4$) 2935, 1590, 1455, 1410, 1215 cm$^1$ The isoxazole was crystallized as the hydrochloride salt: $^1$H NMR (MeOD) δ 2.08 (m, 1H), 2.15 (s, 3H), 2.45 (m, 5H), 2.84 (s, 3H), 3.68 (m, 1H), 3.88 (m, 1H), 4.07 (m, 1H), 4.22 (m, 1H), 5.97 (s, 1H), 7.0 (m, 4H), 7.33 (m, 3H), 7.54 (m, 2H); mp 270–295° C. (dec); Anal calcd for $C_{24}H_{27}ClN_2O$; C=72.99, H=6.89, N=7.10, Cl=8.98; found C=72.91, H=6.91, N=7.15, Cl=8.98; [α]$_D$-102.22 (c=0.68, MeOH)

Example 20
3β-(4-Iodophenyl)-2β-(3-phenylisoxazol-5-yl)tropane Hydrochloride (RTI-181)

Reaction of 0.73 g (1.9 mmol) of 30-(4-Iodophenyl)-2β-(carbomethoxy)tropane as described above for RTI-181 gave after workup 1.46 g of crude isoxazole. Purification of the crude by flash column chromatography [20% (ether/triethylamine 9:1) in hexane] gave 0.5 g (56%) of pure isoxazole RTI-181 which was further purified by crystallizing from methylene chloride/hexane: $^1$H NMR (CDCl$_3$) δ 1.72 (m, 3H), 2.15 (m, 2H), 2.28 (s, 3H), 3.22 (m, 2H), 3.35 (m, 2H), 6.74 (m, 2H), 6.79 (s, 1H), 7.44 (m, 5H), 7.75 (m, 2H); IR (CHCl$_3$) 2940, 1580, 1480, 1475, 1450, 1400, 1355, 1005 cm$^{-1}$ The isoxazole was crystallized as the hydrochloride salt: 1 H NMR (MeOD) δ 2.54 (m, 6H), 2.92 (s, 3H), 3.79 (m, 1H), 4.05 (m, 1H), 4.19 (m, 1H), 4.33 (m, 1H), 6.18 (s, 1H), 7.02 (m, 2H), 7.43 (m, 3H), 7.63 (m, 4H); mp>267° C. (dec); Anal calcd for $C_{23}H_{24}ClIN_2O\cdot0.5H_2O$ C=53.55, H=4.89, N=5.43, Cl=13.75; I=49.21: found C=53.75, H=4.87, N=5.41, Cl=13.68; I=48.95; [α]$_D$-91.11° (c=0.43, MeOH)

Example 21
Biochemistry of 3β-(Substituted phenyl)-2β-(heterocyclic)tropanes Inhibition of radioligand binding data at the dopamine, serotonin, and norepinephrine transporters are listed in Tables II, III and IV.

TABLE II

3β-(Substituted phenyl)-2β-(heterocyclic)tropanes

| Code Name | Het | X | DA [$^3$H]-WIN 35,428 | NE [$^3$H]-nisoxetine | 5-HT [$^3$H]-paroxatine | NE/DA Ratio | 5-HT/DA Ratio |
|---|---|---|---|---|---|---|---|
| RTI-163 | H | Cl | 911 ± 6.1 | 17,386 ± 2050 | 5456 ± 64 | 19 | 6 |
| RTI-157 | | CH$_3$ | 1557 ± 196 | 32,478 ± 2078 | 43,574 ± 5420 | 21 | 28 |

TABLE II-continued

3β-(Substituted phenyl)-2β-(heterocyclic)tropanes

| Code Name | Het | X | DA [³H]-WIN 35,428 | NE [³H]-nisoxetine | 5-HT [³H]-paroxatine | NE/DA Ratio | 5-HT/DA Ratio |
|---|---|---|---|---|---|---|---|
| | | | IC₅₀ (nM) | | | | |
| RTI-165 | 5-methyl-isoxazol-3-yl | Cl | 0.59 ± 0.04 | 181 ± 12 | 572 ± 58 | 307 | 970 |
| RTI-171 | | CH₃ | 0.93 ± 0.09 | 254 ± 31 | 3818 ± 346 | 273 | 4105 |
| RTI-180 | | I | 0.73 ± 0.04 | 67.9 ± 5.25 | 36.4 ± 5.0 | 93 | 498 |
| RTI-177 | 5-phenyl-isoxazol-3-yl | Cl | 1.28 ± 0.18 | 504 ± 29 | 2418 ± 136 | 393 | 1889 |
| RTI-176 | | CH₃ | 1.58 ± 0.02 | 398 ± 18 | 5110 ± 187 | 251 | 3234 |
| RTI-181 | | I | 2.57 ± 0.14 | 868 ± 95 | 100 ± 9.0 | 337 | 39 |
| RTI-189 | 2-methyl-5-phenyl-oxazol-yl | Cl | 19.7 ± 1.98 | 496 ± 42 | 1116 ± 107 | 25 | 57 |
| RTI-178 | | CH₃ | 35.4 ± 1.74 | 677 ± 68 | 1699 ± 167 | 19 | 48 |
| RTI-188 | 2-methyl-5-phenyl-1,3,4-oxadiazolyl | Cl | 12.6 ± 1.03 | 929 ± 88 | 3304 ± 196 | 73 | 262 |
| RTI-195 | | CH₃ | 47.5 ± 4.76 | 1310 ± 37 | 23,310 ± 822 | 28 | 491 |
| RTI-194 | 2,5-dimethyl-1,3,4-oxadiazolyl | CH₃ | 4.45 ± 0.12 | 253 ± 19 | 4885 ± 155 | 57 | 1098 |
| RTI-200 | 2-methyl-5-phenyl-1,3,4-thiadiazolyl | Cl | 15.3 ± 2.43 | 4142 ± 466 | 18,417 ± 1509 | 271 | 1203 |
| RTI-199 | | CH₃ | 35.9 ± 3.4 | 24,321 ± 3822 | 51,460 ± 4513 | 677 | 1434 |
| RTI-202 | 2-benzothiazolyl | Cl | 1.37 ± 0.14 | 403 ± 30 | 1119 ± 120 | 294 | 817 |
| RTI-219 | 2-methyl-5-phenyl-thiazolyl | Cl | 571 ± 0.36 | 8563 ± 824 | 10,342 ± 76 | 1500 | 1811 |

TABLE III

Comparison of Transporter Binding Potencies

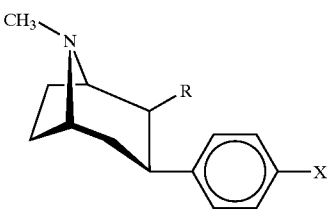

| | | | IC$_{50}$ (Nm) | | |
|---|---|---|---|---|---|
| RTI No. | $R_1$ | $R_2$ | 5-HT [$^3$H] Paroxetine | DA [$^3$H] WIN 35,428 | NE [$^3$H] Nisoxetine |
| 279 | CH$_3$ | CH$_3$ | 1.06 ± 0.39 | 5.98 ± 0.48 | 74.3 ± 3.8 |
| 353 | C$_2$H$_5$ | CH$_3$ | 0.69 ± 0.07 | 331 ± 17 | 148 ± 9.2 |
| Paroxetine* | | | 0.28 ± 0.02 | 623 ± 25 | 313 |

5-HT = serotonin
DA = dopamine
NE = norepinephrine
*Aropax: Seroxat; see Merck Index.

TABLE IV

3β-(Substituted phenyl)-2β-(substituted)tropanes

| | | | IC$_{50}$ (nM) | | |
|---|---|---|---|---|---|
| Code Name | R | X | DA [$^3$H]-WIN 35,428 | NE [$^3$H]-nisoxetine | 5-HT [$^3$H]-paroxetine |
| RTI-93 | CH$_2$OH | Cl | 1.53 ± 0.15 | 43.8 ± 6.4 | 204 ± 16 |
| RTI-99 | CH$_2$OH | Br | 1.49 ± 0.06 | | 51 ± 4.6 |
| RTI-100 | CH$_2$OH | F | 47 ± 4.6 | | 4741 ± 335 |
| RTI-101 | CH$_2$OH | I | 2.2 ± 0.19 | | 26 ± 3.2 |
| RTI-102 | CO$_2$H | I | 474 ± 57 | 43,400 ± 5500 | 1928 ± 120 |
| RTI-103 | CO$_2$H | Br | 278 ± 43 | 17,400 ± 1400 | 3070 ± 208 |
| RTI-104 | CO$_2$H | F | 2744 ± 141 | >100,000 | >100.00 |
| RTI-105 | CH$_2$OAc | Cl | 1.80 ± 0.05 | 127 ± 5.9 | 143 ± 25 |
| RTI-108 | CH$_2$Cl | Cl | 2.64 ± 0.31 | 129 ± 15 | 98 ± 8.7 |
| RTI-123 | CH$_2$OCOC$_6$H$_5$ | Cl | 1.78 ± 0.09 | 393 ± 30 | 3.53 ± 0.58 |
| RTI-131 | CH$_2$NH$_2$ | CH$_3$ | 10.5 ± 1.7 | 120 ± 20 | 855 ± 52 |
| RTI-132 | CH$_2$N(CH$_3$)$_2$ | CH$_3$ | 3.48 ± 0.11 | 137 ± 11 | 208 ± 18 |
| RTI-139 | CH$_3$ | Cl | 1.87 ± 0.13 | 57 ± 2.6 | 85 ± 9.3 |
| RTI-145 | CH$_2$OCO$_2$CH$_3$ | Cl | 9.6 ± 0.42 | 1478 ± 96 | 2930 ± 181 |
| RTI-158 | CN | CH$_3$ | 57 ± 7.3 | 1624 ± 136 | 5095 ± 315 |
| RTI-161 | CN | Cl | 13.1 ± 0.78 | 2516 ± 253 | 1887 ± 134 |
| RTI-164 | CH$_2$NHCH$_3$ | CH$_3$ | 13.6 ± 2.03 | 280 ± 19 | 2248 ± 94 |
| RTI-230 | —C(CH$_3$)=CH$_2$ | Cl | 1.28 ± 0.17 | 141 ± 18 | 57 ± 50 |
| RTI-239 | CH(CH$_3$)$_2$ | CH$_3$ | 0.61 ± 0.07 | 35.6 ± 2.57 | 114 ± 3.69 |
| RTI-240 | CH(CH$_3$)$_2$ | Cl | 1.38 ± 0.03 | 84.5 ± 3.09 | 38.4 ± 2.31 |
| RTI-241 | CH$_2$CO$_2$CH$_3$ | CH$_3$ | 1.02 ± 0.06 | 124 ± 3.56 | 618 ± 28 |

This invention has been described in both generic terms, and by reference to specific description. No specific description or example is considered binding, unless so identified. Alternate forms and methods will occur to those of ordinary skill in the art, without the exercise of inventive faculty, and remain within the scope of this invention, save as limited by the claims set forth below.

What is claimed is:

1. A compound represented by the formula:

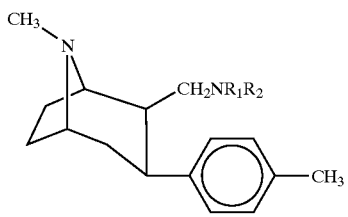

wherein $R_1$ and $R_2$ are, independently, hydrogen or methyl.

2. A compound represented by the formula:

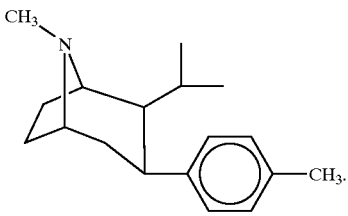

3. A compound represented by the formula:

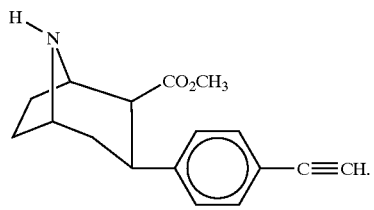

4. A compound represented by the formula:

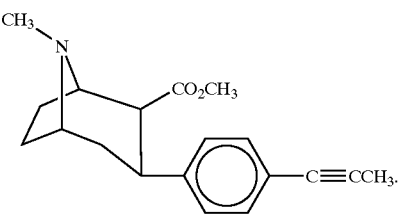

* * * * *